United States Patent
Liu et al.

(10) Patent No.: US 11,173,217 B2
(45) Date of Patent: Nov. 16, 2021

(54) METHODS AND COMPOSITIONS FOR NEAR INFRARED FLUORESCENT NANODOTS WITH AGGREGATION-INDUCED EMISSION CHARACTERISTICS

(71) Applicant: NATIONAL UNIVERSITY OF SINGAPORE, Singapore (SG)

(72) Inventors: Bin Liu, Singapore (SG); Jie Liu, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 0 days.

(21) Appl. No.: 16/324,851

(22) PCT Filed: Aug. 10, 2017

(86) PCT No.: PCT/SG2017/050399
§ 371 (c)(1),
(2) Date: Feb. 11, 2019

(87) PCT Pub. No.: WO2018/030957
PCT Pub. Date: Feb. 15, 2018

(65) Prior Publication Data
US 2019/0358350 A1 Nov. 28, 2019

(30) Foreign Application Priority Data
Aug. 12, 2016 (SG) .............................. 10201606719P

(51) Int. Cl.
*C09B 23/14* (2006.01)
*A61K 49/00* (2006.01)
*C09K 11/06* (2006.01)

(52) U.S. Cl.
CPC ...... *A61K 49/0093* (2013.01); *A61K 49/0021* (2013.01); *C09B 23/141* (2013.01); *C09K 11/06* (2013.01); *C09K 2211/1018* (2013.01)

(58) Field of Classification Search
None
See application file for complete search history.

(56) References Cited

U.S. PATENT DOCUMENTS

| | | |
|---|---|---|
| 2012/0237964 A1 | 9/2012 | Tang et al. |
| 2014/0212359 A1 | 7/2014 | Tang et al. |
| 2014/0328764 A1 | 11/2014 | Tang et al. |

FOREIGN PATENT DOCUMENTS

| | | |
|---|---|---|
| CN | 102276414 A | 12/2011 |
| CN | 103788940 A | 5/2014 |
| WO | 2013/029340 A9 | 7/2013 |
| WO | 2015/163817 A1 | 10/2015 |

OTHER PUBLICATIONS

Du, Xiaobo. Efficient Non-doped Near Infrared Organic Light-Emitting Devices Based on Fluorophores with Aggregation-Induced Emission Enhancement. Chem. Mater. 24, 2012, 2178-2185.*
International Search Report corresponding to PCT/SG2017/050399 dated Nov. 3, 2017; 6 pages.
Written Opinion of the International Searching Authority corresponding to PCT/SG2017/050399 completed Oct. 18, 2017; 6 pages.
Du, X. et al., "Efficient Non-doped Near Infrared Organic Light-Emitting Devices Based on Fluorophores with Aggregation-Induced Emission Enhancement," *Chemistry of Materials* (May 22, 2012); vol. 24, No. 11, pp. 2178-2185.
Jana, D. et al., "Pyridine-cored V-shaped Tr-conjugated oligomers: synthesis and optical properties," *Tetrahedron* (Jun. 29, 2012); vol. 68, No. 36, pp. 7309-7316.
Jana, D. et al., "Synthesis of gem-tetraphenylethylene oligomers utilizing Suzuki reaction and their aggregation properties," *Dyes and Pigments* (Jul. 15, 2013); vol. 99, No. 3, pp. 740-747.
Wan, Q. et al., "Preparation of Ultrabright AIE Nanoprobes via Dynamic Bonds," *Tetrahedron* (Sep. 25, 2015); vol. 71, No. 46, pp. 8791-8797.
International Preliminary Report on Patentability corresponding to PCT/SG2017/050399 dated Feb. 12, 2019; 7 pages.
Azael Gomez-Duran et al., "Effect of AIE Substituents on the Fluorescence of Tetraphenylethene-Containing BODIPY Derivatives," ACS Appl. Mater. Interfaces, 7, pp. 15168-15176 (2015).
Li et al., "Biocompatible organic dots with aggregation-induced emission for in vitro and in vivo fluorescence imaging," *Sci. China Chem.*, 56, pp. 1228-1233 (2013).
Li et al., "Synthesis and Characterization of Near-Infrared Absorbing and Fluorescent Liquid-Crystal Chromophores," Organic Letters, 10(17), pp. 3785-3787 (2008).
Qian et al., "Simple and Efficient Near-Infrared Organic Chromophores for Light-Emitting Diodes with Single Electroluminescent Emission above 1000 nm,"Adv. Mater., 21, pp. 111-116 (2009).
Rananaware et al., "Construction of a highly efficient near-IR solid emitter based on naphthalene diimide with AIEactive tetraphenylethene periphery," RSC Adv., 6, pp. 16250-16255 (2016).
Wang and Yan, "Superior asymmetric supercapacitor based on Ni-Co oxide nanosheets and carbon nanorods," Scientific Reports 4(3712), pp. 1-9 (2014).
Wang et al., "Red emissive AIE nanodots with high two-photon absorption efficiency at 1040 nm for deep-tissue in vivo imaging," Biomedical Optics Express, 6(10), pp. 3783-3794 (2015).

* cited by examiner

*Primary Examiner* — Samantha L Shterengarts
(74) *Attorney, Agent, or Firm* — Mintz, Levin, Cohn, Ferris, Glovsky and Popeo, P.C.

(57) ABSTRACT

Disclosed herein is a donor-acceptor-donor (D-A-D) compound of formula I, where in the acceptors are mono-substituted tetraphenylethylene moieties. Also disclosed herein are fluorescent nanodots that comprise the compound of formula (I) and uses of said compound or nanodots in in vivo imaging or detecting of cancer cells in a subject.

14 Claims, 9 Drawing Sheets

METHODS AND COMPOSITIONS FOR NEAR INFRARED FLUORESCENT NANODOTS WITH AGGREGATION-INDUCED EMISSION CHARACTERISTICS

FIELD OF INVENTION

The current application relates to a series of far-red excitable near infrared fluorescent nanodots with aggregation-induced emission characteristics (AIE). The current application further describes compounds suitable as far-red excitable NIR fluorescent AIE chromophores and methods of nanodot fabrication using said chromophores. The AIE-dots may be used as fluorescent agents for NIR fluorescence image-guided tumor surgery.

BACKGROUND

The listing or discussion of an apparently prior-published document in this specification should not necessarily be taken as an acknowledgement that the document is part of the state of the art or is common general knowledge.

Fluorescence imaging technology has opened new avenues for the development of cancer diagnosis and therapeutics. Fluorescence imaging probes with intense emission in the near-infrared (NIR) region are attracting increasing attention due to their ability to overcome the interferences of optical absorption, light scattering and auto-fluorescence of biological media.

Problems associated with conventional organic dyes (e.g. indocyanine green (ICG)) include problems with photostability and the quenching of fluorescence caused by aggregation. These problems are also associated with many other fluorescence probes and so there remains a need for improved fluorescence probes that overcome these problems.

SUMMARY OF INVENTION

Provided herein are far-red excitable near infrared fluorescent molecules with aggregation-induced emission (AIE) characteristics for bioimaging, for example in vivo bioimaging.

Also provided herein are compounds suitable for use in the preparation of near infrared (NIR) fluorescent nanodots and methods of fabricating the same, where the compounds have aggregation-induced emission (AIE) characteristics and so provide nanodots with said properties (AIE-dots). The said AIE-dots may be used as fluorescent agents for NIR fluorescence imaging. The designed chromophores may have a donor-acceptor-donor (D-A-D) structure and peripheral mono-substituted tetraphenylethenes (TPE). Without wishing to be bound by theory, it is believed that the substituents bonded to the TPE groups and the D-A-D structure operate in conjunction to, e.g., improve solubility, reduce the intermolecular interaction in aggregated states and blue-shift the emission compared to comparative di-substituted TPE D-A-D NIR molecules.

Aspects and embodiments of the current disclosure are described with reference to the numbered clauses hereinbelow.

1. A compound of structural formula I:

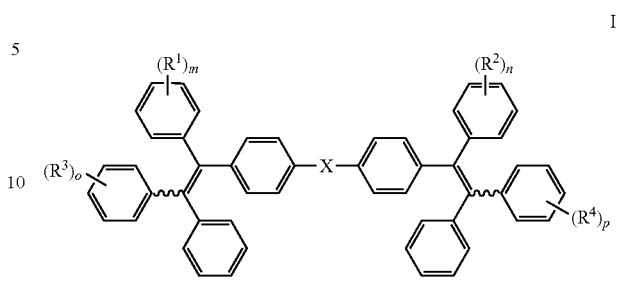

I wherein,
X represents an acceptor moiety;
$R^1$ and $R^2$ independently represent $OR^5$ or $C_{1-21}$ alkyl;
$R^3$ and $R^4$ independently represent $OR^6$ or $C_{1-21}$ alkyl;
$R^5$ and $R^6$ independently represent $C_{1-21}$ alkyl;
m and n represent 0 or 1; and
o and p represent 0 or 1, provided that:
when m and n represent 0, o and p represent 1; and
when o and p represent 0, m and n represent 1.

2. The compound of Clause 1, where X is selected from one or more of the group consisting of:

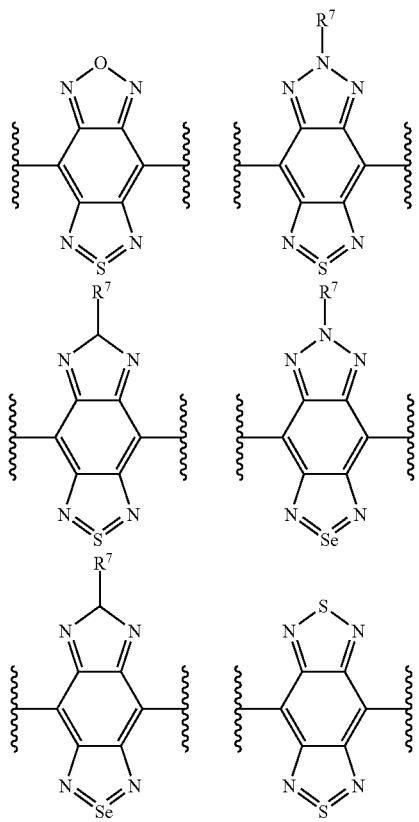

where each wavy line represents a point of attachment to the rest of the compound, and $R^7$ represents $C_{1-21}$ alkyl.

3. The compound of Clause 1 or Clause 2, wherein, when present, each of $R^1$ to $R^4$ are attached to its respective phenyl ring in the ortho- or para-position relative to the point of attachment of said phenyl ring to the rest of the compound.

4. The compound of Clause 3, wherein, when present, each or $R^1$ to $R^4$ are attached to its respective phenyl ring in the para-position relative to the point of attachment of said phenyl ring to the rest of the compound.

5. The compound of any one of the preceding clauses, wherein, when present, $R^1$ to $R^4$ and $R^7$ independently represent $C_{1-18}$ alkyl.

6. The compound of Clause 5, wherein, when present, $R^1$ to $R^4$ and $R^7$ independently represent $C_{2-15}$ alkyl (e.g. $C_{4-12}$ alkyl).

7. The compound of any one of Clauses 1 to 4, wherein, when present, $R^5$ to $R^7$ independently represent $C_{1-18}$ alkyl.

8. The compound of Clause 7, wherein, when present, $R^5$ to $R^7$ independently represent $C_{2-15}$ alkyl (e.g. $C_{4-12}$ alkyl).

9. The compound of any one of the Clauses 1 to 4, 7 and 8, wherein $R^1$ and $R^2$ are both $OR^5$ and $R^3$ and $R^4$ are both H.

10. The compound of any one of the preceding clauses, wherein the compound has structural formula II:

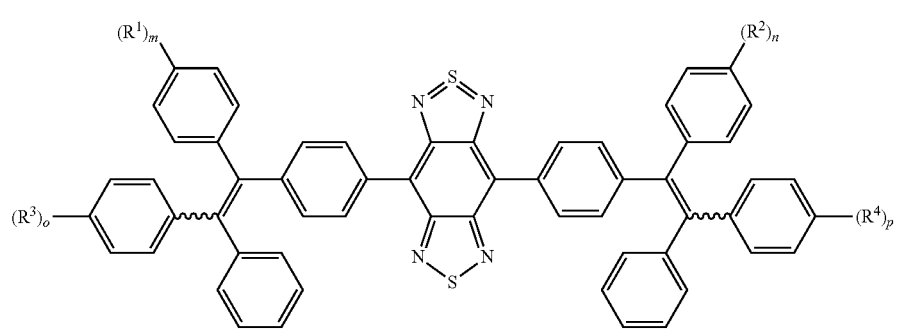

II wherein, $R^1$ to $R^4$, m, n, o and p are as defined in Clause 1.

11. The compound of any one of Clauses 1 to 4, and 7 to 9, wherein the compound is selected from:

i)
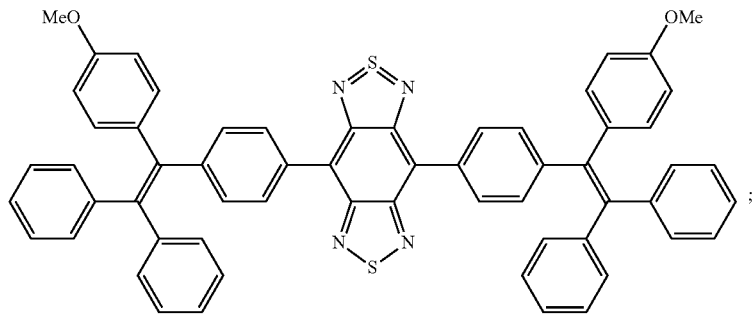
;

ii)
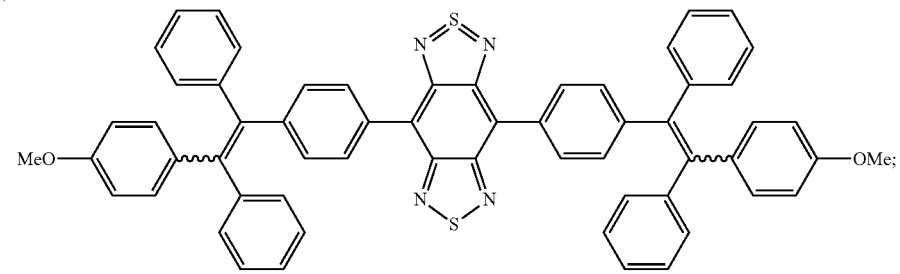
;

iii)
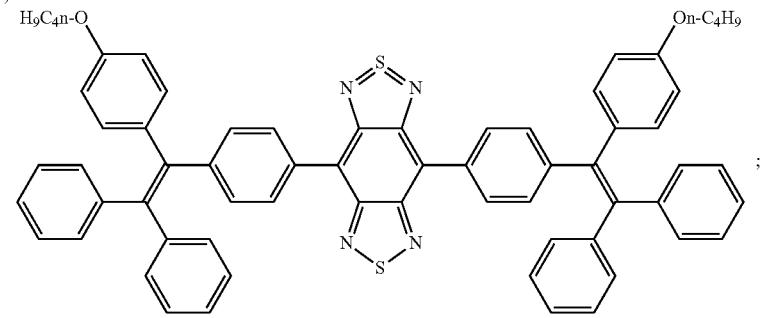
;

iv)
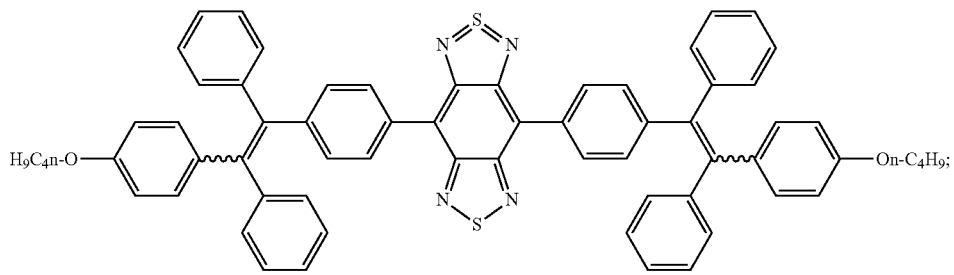
v)
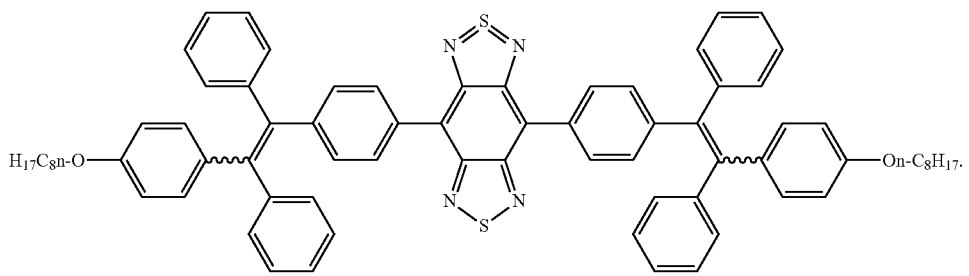
and
vi)
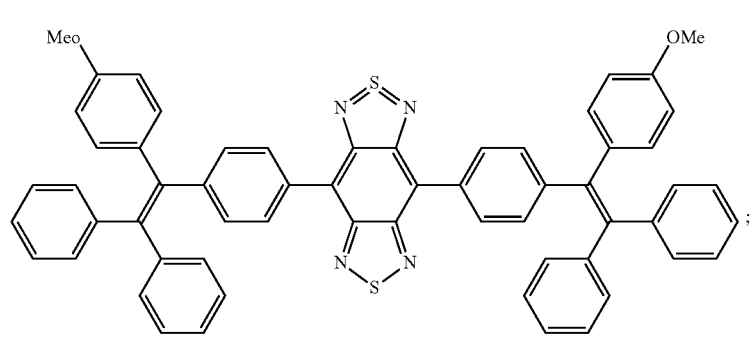
12. The compound of Clause 11, wherein the compound is selected from:
i)

-continued

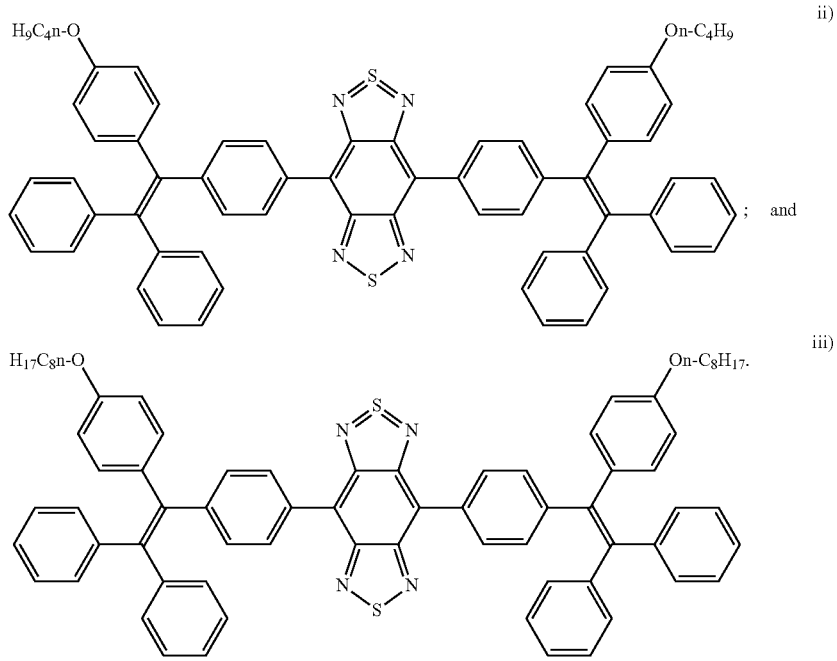

13. Fluorescent nanodots comprising a compound of any one of Clauses 1 to 12, wherein the nanodots have a diameter of from 5 nm to 500 nm.
14. The nanodots according to Clause 13, wherein the nanodots further comprise a carrier material and the compound is provided in the form of aggregated particles encapsulated within the carrier material.
15. The nanodots according to Clause 13 or Clause 14, wherein the carrier material is selected from one or more of the group selected from lipids, polyethylene glycol, chitosan, polyvinyl alcohol, poly(2-hydroxyethylmethacrylate), bovine serum albumin, silica, polystyrene, blends thereof, and congugates thereof (e.g. is selected from one or more of the group selected from phospholipids, polyethylene glycol, silica, polystyrene, blends thereof, and congugates thereof, such as a phospholipid-polyethylene glycol conjugate, silica, or a silica-polystyrene conjugate or blend).
16. The nanodots according to any one of Clauses 13 to 15, wherein:
    (a) the nanodots have a fluorescence emission peak at from around 800 nm to 820 nm (e.g. from 801 nm to 815 nm); and/or
    (b) the nanodots have a quantum yield of from 2% to 10%; and/or
    (c) the nanodots have a Stokes shift of greater than or equal to 100 nm (e.g. from 100 nm to 200 nm).
17. A pharmaceutical composition comprising a compound according to any one of Clauses 1 to 12 or fluorescent nanodots according to any one of Clauses 13 to 16 and a pharmaceutically acceptable carrier.
18. The compound according to any one of Clauses 1 to 12, the fluorescent nanodots according to any one of Clauses 13 to 16, or the composition according to Clause 17 for use as an imaging agent (e.g. in fluorescence imaging) for detecting cancer cells in a subject.
19. The compound according to any one of Clauses 1 to 12, the fluorescent nanodots according to any one of Clauses 13 to 16, or the composition according to Clause 17 for use in the preparation of an in vivo imaging agent for detecting cancer cells in a subject.
20. A method for detecting cancer cells in a subject comprising administering an effective amount of the compound according to any one of Clauses 1 to 12, the fluorescent nanodots according to any one of Clauses 13 to 16, or the composition according to Clause 17 to the subject, and imaging the subject with a molecular imaging device to detect the compound or composition in the subject.
21. The compound according to Clause 18, the use according to Clause 19 or the method according to Clause 20, wherein:
    (a) the compound, nanodots or composition specifically accumulates in cancer cells relative to non-cancer cells; and/or
    (b) detection of the compound, nanodots or composition in an organ of the subject is an indication that cancers cells are present in the organ; and/or
    (c) the cancer cells are lung cancer, breast cancer, prostate cancer, cervical cancer, pancreatic cancer, colon cancer, ovarian cancer, stomach cancer, esophagus cancer, skin cancer, heart cancer, liver cancer, bronchial cancer, testicular cancer, kidney cancer, bladder cancer, spleen cancer, thymus cancer, thyroid cancer, brain cancer, or gall bladder cancer cells; and/or
    (d) the compound, nanodots or composition is detected using an optical imaging device.

DRAWINGS

Certain embodiments of the present disclosure are described more fully hereinafter with reference to the accompanying drawings.

FIG. 1 schematically depicts a molecular design concept of far-red excitable NIR fluorescent AIE molecules and their chemical structures.

FIG. 2 schematically depicts synthetic routes of compounds α-DTPEBDBBTD-Cx and β-DTPEBBTD-Cx, where the x represents the carbon numbers of the alkoxy chains. Reagents and conditions: a) 4-bromobenzophenone, zinc, $TiCl_4$, THF (tetrahydrofuran); b) $BBr_3$, $CH_2Cl_2$; c) $Cs_2CO_3$, DMF, room temperature, 1-bromobutane for 3a and 8a, 1-bromooctane for 3b and 8b; d) BuLi, $Me_3SnCl$, THF, −78° C., overnight; e) dibromoBBTD, $Pd(PPh_3)_4$, toluene, 100° C., 24 h; f) 4-bromobenzoyl chloride, $AlCl_3$, $CH_2Cl_2$; g) diphenylmethane, n-BuLi, THF.

FIGS. 3A-F depict photoluminescence spectra and plots of the relative PL intensity compounds for α-DT-PEBDBBTD-Cx and β-DTPEBBTD-Cx in THF/$H_2O$ mixtures with different volume fractions of water ($f_w$). $\lambda_{ex}$=635 nm, where the x in Cx refers to the number of carbon atoms in the alkoxy chain and where x is 1, 4 or 8. The concentration is 5 µM.

FIG. 4A provides a schematic illustration of AIE nanoparticles (NPs) preparation. FIG. 4B depicts representative LLS and TEM results of AIE-dots. FIGS. 4C-D depict UV-vis absorption and PL spectra of these AIE-dots in water, respectively. FIG. 4E graphically depicts quantum yields of AIE-dots in water.

FIG. 9A depicts bioluminescence and FIG. 9B depicts fluorescence images of peritoneal carcinomatosis-bearing mice after intravenous injection of AIE-dots for 24 hours. The arrows indicate sub-millimeter tumors in the peritoneal cavity. FIG. 9C shows the average fluorescence intensity of tumors and surrounding normal tissues from AIE-dot-treated mice. The error bars were based on 5 mice.

DESCRIPTION

Figure 1:
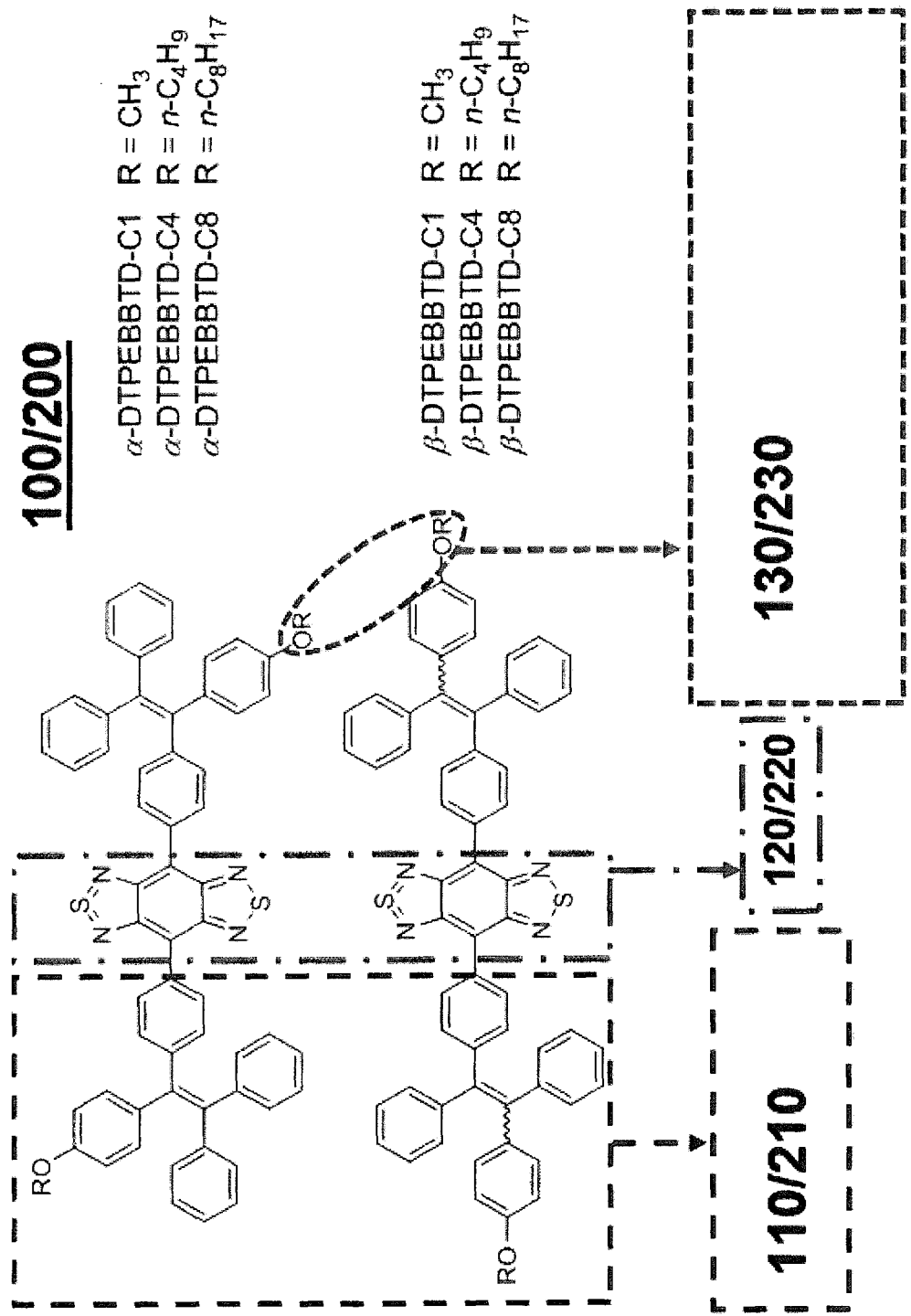

To obtain far-red excitable NIR fluorescent chromophores, molecules having donor-acceptor-donor (D-A-D) structures 100/200 exemplified in FIG. 1 were prepared, in which the peripheral monoalkoxy-substituted tetraphenylethenes (monoalkoxy-substituted TPEs) act as donor and AIE-enabling units 110/210 attached to an acceptor unit 120/220, where the inclusion of the alkoxy groups 130/230 may help to improve solubility, reduce intermolecular interaction and assist in tuning the emission maximum. Additionally, it has been surprisingly found that these compounds, which have mono-substituted donor groups (e.g., mono-alkoxy and mono-alkyl), have improved solubility, reduced intermolecular interactions in aggregated states and are blue-shifted in the emission spectrum compared to dual-alkoxy-substituted NIR molecules (that is molecules where each donor group has two alkoxy substituents). Thus, there is provided a compound of structural formula I:

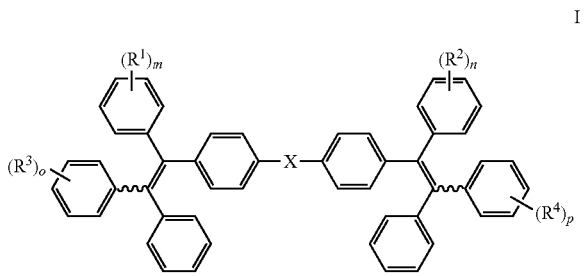

I wherein,
X represents an acceptor moiety;
$R^1$ and $R^2$ independently represent $OR^5$ or $C_{1-21}$ alkyl;
$R^3$ and $R^4$ independently represent $OR^6$ or $C_{1-21}$ alkyl;
$R^5$ and $R^6$ independently represent $C_{1-21}$ alkyl;
m and n represent 0 or 1; and
o and p represent 0 or 1, provided that:
when m and n represent 0, o and p represent 1; and
when o and p represent 0, m and n represent 1.

References herein (in any aspect or embodiment of the present disclosure) to compounds of formula I or formula II includes references to such compounds per se, to isomers of such compound and to tautomers of such compounds.

Compounds of formula I may contain double bonds and may thus exist as E (entgegen) and Z (zusammen) geometric isomers about each individual double bond. All such isomers and mixtures thereof are included within the scope of the present disclosure. As such, in compounds of formula I where o and p represent 1, the wiggly bonds denote cis- and/or trans-stereochemistry, where the two donor groups have the same (i.e. both cis- or both trans-) or different (i.e. one cis- and the other trans-) stereochemistry. For example, when o and p represent 1 and $R^3$ and $R^4$ represent $OCH_3$ in the para-position, relative to the point of attachment of the benzene ring it is attached on to the rest of the molecule, the following molecules are intended to be covered.

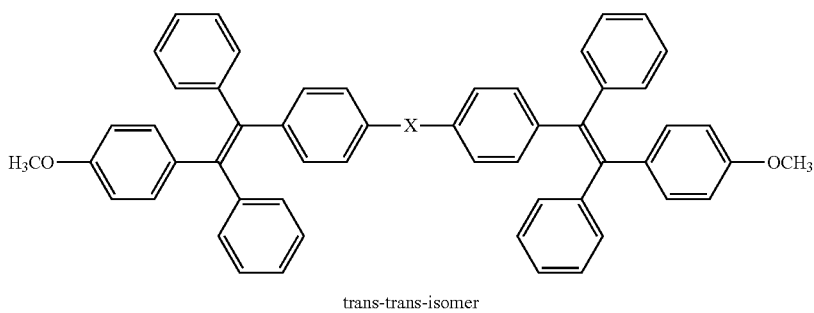

trans-trans-isomer

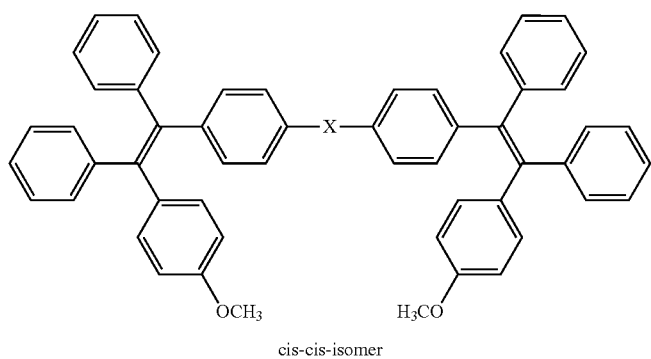

cis-cis-isomer

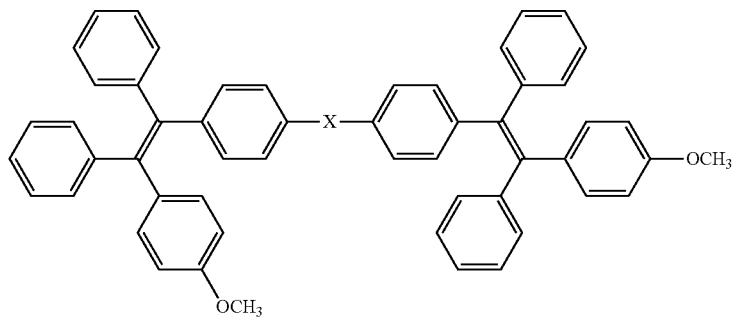

cis-trans-isomer

For the purposes of the current disclosure "cis-" is defined as having the substituent on the benzene ring on the same side of the carbon to carbon double bond as the benzene ring attached to the acceptor moiety, while "trans-" is defined as having the substituent on the benzene ring on the opposite side of the carbon to carbon double bond as the benzene ring attached to the acceptor moiety.

In compounds of formula I where m and n represent 1, the wiggly bonds are single bonds and do not denote any stereochemistry.

Unless otherwise stated, the term "alkyl" refers to saturated or unsaturated (so forming, for example, an alkenyl or alkynyl) cyclic or acyclic hydrocarbyl radical, which may be substituted or unsubstituted (with, for example, one or more halo atoms). Where the term "alkyl" refers to an acyclic group, it may be a branched or unbranched (i.e., linear) $C_{1-21}$ alkyl, such as $C_{1-18}$ alkyl or $C_{2-15}$ alkyl (e.g. $C_{4-12}$ alkyl). Where the term "alkyl" is, a cyclic group, it may be a $C_{3-12}$ cycloalkyl and, more preferably, $C_{5-10}$ (e.g. $C_{5-7}$) cycloalkyl. It will be appreciated that the alkyl group may incorporate both acyclic and cyclic components and may be an alkyl group having a total number of carbon atoms of from 4 to 21, such as from 4 to 18 or 5 to 15 (e.g. 6 to 12), where there may be one or more cyclic alkyl groups as defined herein connected to one or more acyclic alkyl groups. When "alkyl" relates to a group that incorporates both acyclic and cyclic components it will be appreciated that any suitable combination thereof is specifically covered herein.

Suitable acceptor moieties (that is, suitable X groups that may be mentioned herein) include the following structural fragments:

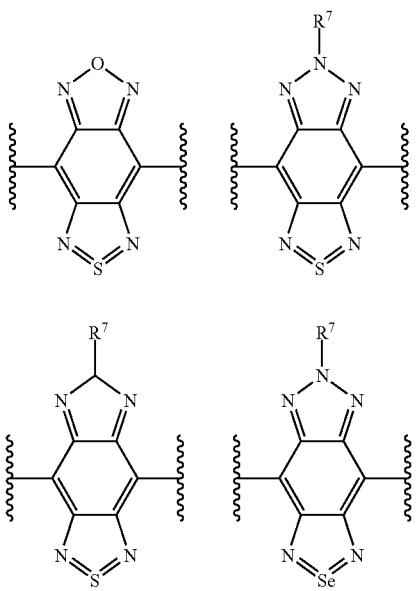

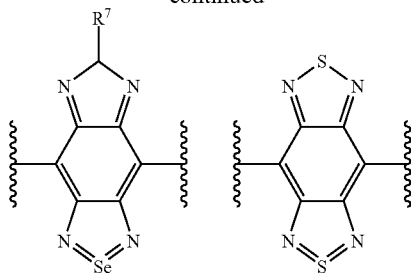

where each wavy line represents a point of attachment to the rest of the compound, and $R^7$ represents $C_{1-21}$ alkyl.

In certain embodiments, $R^7$ is selected from the group consisting of $C_{1-19}$; $C_{1-17}$; $C_{1-15}$; $C_{1-13}$; $C_{1-11}$; $C_{1-9}$, $C_{1-7}$, $C_{1-5}$, $C_{1-3}$, $C_{1-19}$, $C_{3-19}$, $C_{5-19}$, $C_{7-19}$, $C_{9-19}$, $C_{11-19}$, $C_{13-19}$, $C_{15-19}$, and $C_{17-19}$ alkyl. In certain embodiments, $R^7$ is selected from the group consisting of $C_{5-19}$, $C_{10-19}$, $C_{15-19}$, $C_{1-15}$, $C_{1-10}$, and $C_{1-5}$ alkyl.

In certain embodiments, when present, each of $R^1$ to $R^4$ may be attached to its respective phenyl ring in the ortho- or para-position relative to the point of attachment of said phenyl ring to the rest of the compound. For example, each of $R^1$ to $R^4$ may be attached to its respective phenyl ring in the para-position relative to the point of attachment of said phenyl ring to the rest of the compound.

In certain embodiments, $R^1$, $R^2$, $R^3$ and $R^4$ are independently selected from the group consisting of $C_{1-21}$; $C_{2-21}$, $C_{3-21}$, $C_{5-21}$, $C_{5-19}$, $C_{5-17}$, $C_{5-15}$, $C_{5-13}$, $C_{5-11}$, $C_{6-11}$, and $C_{6-10}$ alkyl.

In certain embodiments, $R^1$, $R^2$, $R^3$ and $R^4$ are each linear alkanes. In certain embodiments, $R^1$, $R^2$, $R^3$ and $R^4$ are independently selected from the group consisting of n-$C_{1-21}$, n-$C_{2-21}$, n-$C_{3-21}$; n-$C_{5-21}$; n-$C_{5-19}$; n-$C_{5-17}$; n-$C_{5-15}$; n-$C_{5-13}$; n-$C_{5-11}$; n-$C_{6-11}$; and n-$C_{6-10}$ alkyl. In certain embodiments, $R^1$, $R^2$, $R^3$ and $R^4$ are independently selected from the group consisting n-$C_4$, n-$C_5$, n-$C_6$, n-$C_7$, n-$C_5$, n-$C_9$, and n-$C_{10}$.

In certain embodiments, $R^5$ and/or $R^6$ for each instance is independently selected from the group consisting of $C_{1-21}$; $C_{2-21}$, $C_{3-21}$, $C_{6-21}$, $C_{6-10}$, $C_{6-17}$, $C_{6-16}$, $C_{6-13}$, $C_{6-11}$, $C_{6-11}$, and $C_{6-10}$ alkyl.

In certain embodiments, $R^5$ and/or $R^6$ for each instance is a linear alkane. In certain embodiments, $R^6$ for each instance is independently selected from the group consisting of n-$C_{1-21}$; n-$C_{2-21}$; n-$C_{3-21}$; n-$C_{5-21}$; n-$C_{5-19}$; n-$C_{5-17}$; n-$C_{5-15}$; n-$C_{5-13}$; n-$C_{5-11}$; n-$C_{6-11}$; and n-$C_{6-10}$ alkyl. In certain embodiments, $R^5$ and/or $R^6$ for each instance is independently selected from the group consisting of n-$C_4$, n-$C_5$, n-$C_6$, n-$C_7$, n-$C_5$, n-$C_9$, and n-$C_{10}$.

In certain embodiments, when present, $R^1$ to $R^4$ and $R^7$ may independently represent $C_{1-18}$ alkyl (e.g. $C_{2-16}$ alkyl, such as $C_{4-12}$ alkyl). In certain embodiments, when present, $R^5$ to $R^7$ may independently represent $C_{1-18}$ alkyl (e.g. $C_{2-16}$ alkyl, such as $C_{4-12}$ alkyl). In certain embodiments of the invention that may be mentioned herein, $R^1$ and $R^2$ may both be $OR^5$ and $R^3$ and $R^4$ may both be H.

In certain embodiments, the acceptor moeity that may be mentioned herein is benzo[1,2-c;4,5-c']bis[1,2,5]thiadiazole (BBTD). For example, the compound may have the structural formula II:

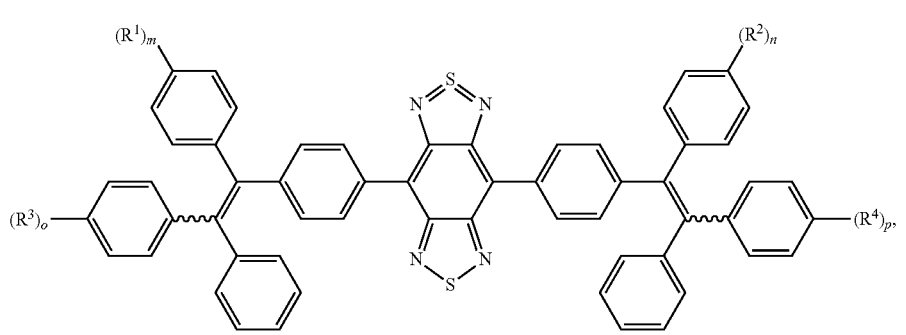

II where $R^1$ to $R^4$, m, n, o and p are as defined hereinbefore (including any technically sensible variation thereof).

In certain embodiments, the compound of structural formula I or structural formula II may be selected from:

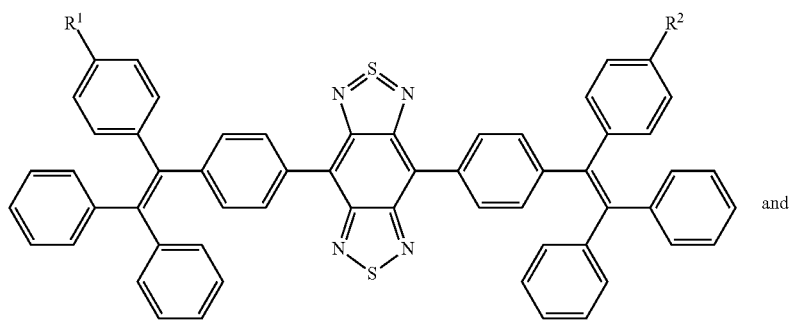

and

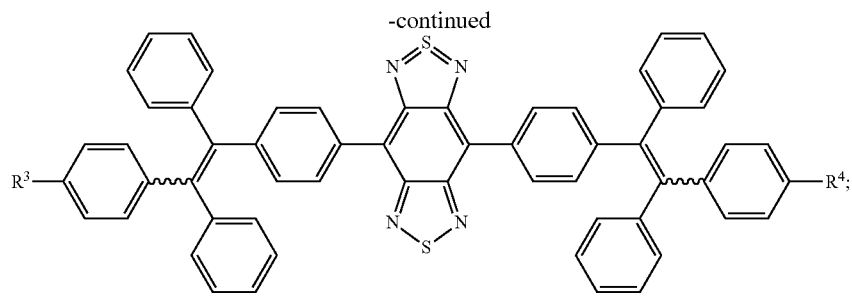

wherein $R^1$ and $R^2$ are independently selected from the group consisting of $C_{1-21}$; $C_{2-21}$; $C_{3-21}$; $C_{5-21}$; $C_{5-19}$; $C_{5-17}$; $C_{5-15}$; $C_{5-13}$; $C_{5-11}$; $C_{6-11}$; and $C_{6-10}$ alkyl; or $R^5$;

$R^3$, and $R^4$ are independently selected from the group consisting of $C_{1-21}$; $C_{2-21}$, $C_{3-21}$, $C_{5-21}$, $C_{5-19}$, $C_{5-17}$, $C_{5-15}$, $C_{5-13}$, $C_{5-11}$, $C_{6-11}$, and $C_{6-10}$ alkyl; or $R^6$; and $R^5$ and/or $R^6$ for each instance is independently selected from the group consisting of n-$C_{1-21}$, n-$C_{2-21}$; n-$C_{3-21}$; n-$C_{5-21}$; n-$C_{5-19}$; n-$C_{5-17}$; n-$C_{5-15}$; n-$C_{5-13}$; n-$C_{5-11}$; n-$C_{6-11}$; and n-$C_{6-10}$ alkyl.

In certain embodiments, the compound of structural formula I or structural formula II may be selected from:

i)

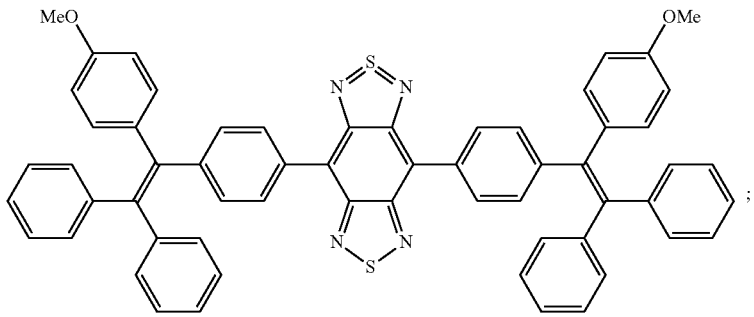

ii)

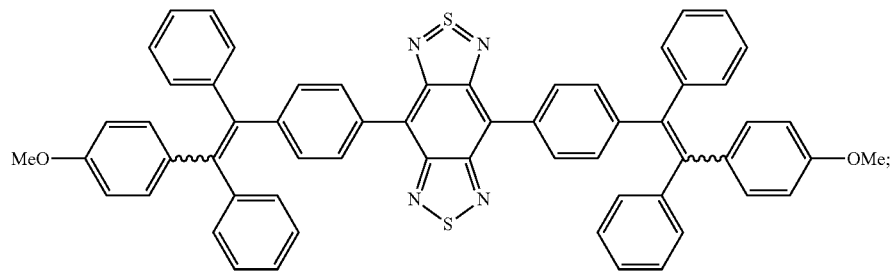

iii)

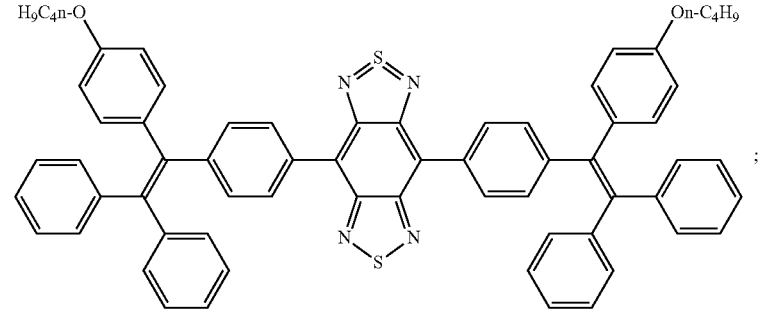

iv)

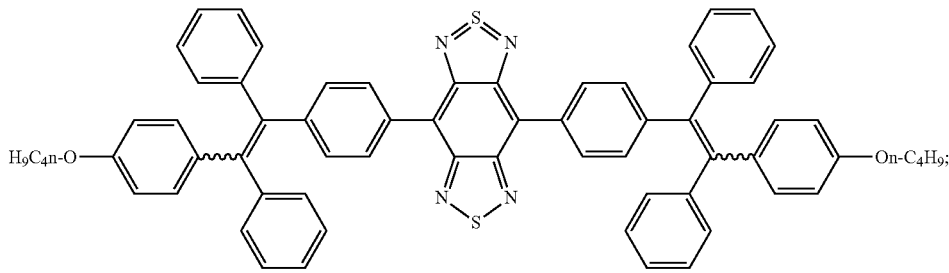

v)

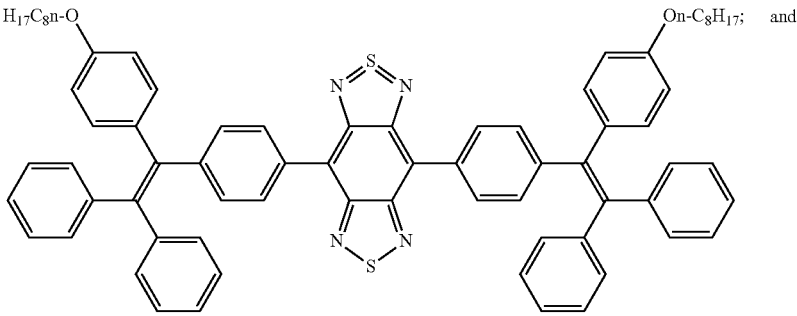

vi)

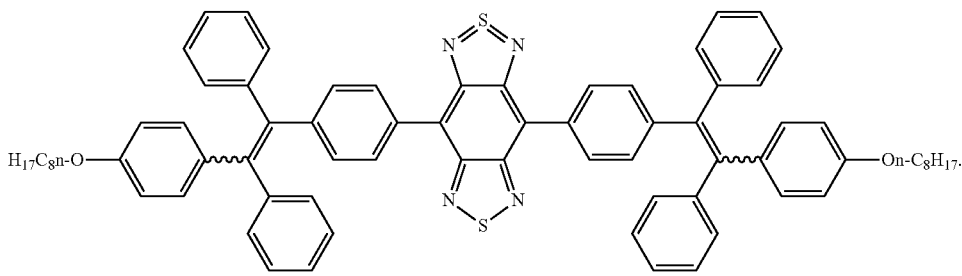

For example, the compound of structural formula I or II may be compound (i), (iii) or (v) of the list above.

In a further aspect, the compounds described hereinbefore may be suitable for application in the manufacture and use of fluorescent nanodots. Thus, the current disclosure also relates to fluorescent nanodots comprising a compound of structural formula I or structural formula II, wherein the nanodots have a diameter of from 5 nm to 500 nm.

When mentioned herein, the diameter of the fluorescent nanodots may be measured by any suitable method. In certain embodiments, the diameter may be measured using transmission electron microscopy, where the measured diameter of the nanodots may be from 5 to 500 nm, such as from 25 to 400 nm, such as from 50 to 250 nm.

In certain embodiments, the nanodots may further comprise a carrier material and the compound may be provided in the form of aggregated particles encapsulated within the carrier material. Suitable carrier materials that may be mentioned herein include one or more of the group selected from lipids, polyethylene glycol, chitosan, polyvinyl alcohol, poly(2-hydroxyethylmethacrylate), bovine serum albumin, silica, polystyrene, blends thereof, and conjugates thereof (e.g. is selected from one or more of the group selected from phospholipids, polyethylene glycol, silica, polystyrene, blends thereof, and conjugates thereof, such as a phospholipid-polyethylene glycol conjugate, silica, or a silica-polystyrene conjugate or blend).

Figure 4:
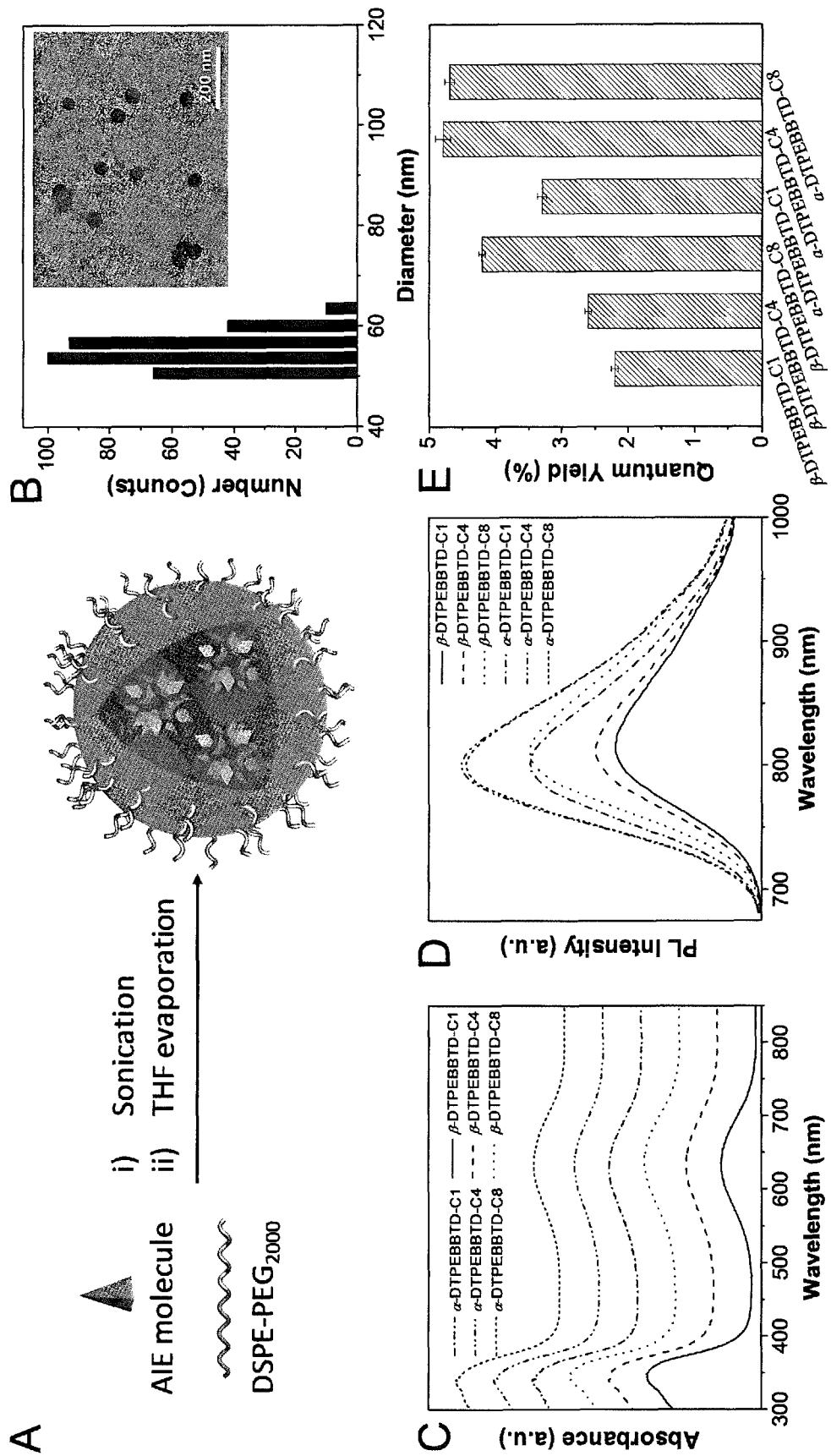

In certain embodiments, the nanodot is prepared by providing amphiphilic 1,2-distearoyl-sn-glycero-3-phosphoethanolamine conjugated polyethylene glycol (DSPE-PEG$_{2000}$) as a matrix and formulating the compounds of structural formula I and/or II into nanodots (AIE-dots) through the nanoprecipitation approach, as set out in more detail in FIG. 4A and the examples.

In certain embodiments, the nanodots may have:
(a) a fluorescence emission peak at from around 800 nm to 820 nm (e.g. from 801 nm to 815 nm); and/or
(b) a quantum yield of from 2% to 10%; and/or
(c) a Stokes shift of greater than or equal to 100 nm (e.g. from 100 nm to 200 nm).

The compound of structural formula I (or II) and fluorescent nanodots that comprise said compounds may be useful in medicine. As such, there is also provided a pharmaceutical composition comprising a compound of formula I (or II) or fluorescent nanodots as described hereinbefore and a pharmaceutically acceptable carrier.

Pharmaceutical compositions comprising the compound of formula I (or II) or fluorescent nanodots as described hereinbefore may be administered by any suitable route, but may particularly be administered orally, intravenously, intramuscularly, cutaneously, subcutaneously, transmucosally (e.g. sublingually or buccally), rectally, transdermally, nasally, pulmonarily (e.g. tracheally or bronchially), topically, by any other parenteral route, in the form of a pharmaceutical preparation comprising the compound in a pharmaceutically acceptable dosage form. Particular modes of administration that may be mentioned include oral, intravenous, cutaneous, subcutaneous, nasal, intramuscular or intraperitoneal administration.

Compounds of formula I (or II) or the nanodots as described hereinbefore will generally be administered as a pharmaceutical composition in admixture with a pharmaceutically acceptable adjuvant, diluent or carrier, which may be selected with due regard to the intended route of administration and standard pharmaceutical practice. Such pharmaceutically acceptable carriers may be chemically inert to the active compounds and may have no detrimental side effects or toxicity under the conditions of use. Suitable pharmaceutical compositions may be found in, for example, Remington *The Science and Practice of Pharmacy*, 19th ed., Mack Printing Company, Easton, Pa. (1995). For parenteral administration, a parenterally acceptable aqueous solution may be employed, which is pyrogen free and has requisite pH, isotonicity, and stability. Suitable solutions will be well known to the skilled person, with numerous methods being described in the literature. A brief review of methods of drug delivery may also be found in e.g. Langer, *Science* (1990) 249, 1527.

Otherwise, the preparation of suitable compositions may be achieved routinely by the skilled person using routine techniques and/or in accordance with standard and/or accepted pharmaceutical practice.

The amount of compound of formula I (or II) or the nanodots as described hereinbefore in any pharmaceutical composition used in accordance with the present disclosure will depend on various factors, such as the severity of the condition, the particular patient to be treated, as well as the compound(s) which is/are employed. In any event, the amount of compound of formula I in the formulation may be determined routinely by the skilled person.

The compounds of the present disclosure (and the nanodots comprising said compounds) may be used in near infrared (NIR) fluorescence imaging for accurate tumor detection and resection, also in NIR fluorescent image-guided cancer surgery. In certain embodiments, the emission maxima of the compounds of the present disclosure are blue-shifted to 800-810 nm, which is preferred for current in-vivo applications, such as diagnosis and surgery. In certain embodiments, the compounds of the present disclosure (and nanodots comprising the same) enables one to tune the AIE properties by changing the number, position and length of the substituted alkoxy chain on TPE blocks, as is illustrated in the non-limiting examples provided hereinbelow.

Thus, there is provided:
(a) a compound of formula I (or II), fluorescent nanodots or a pharmaceutical composition as described hereinbefore for use as an imaging agent (e.g. in fluorescence imaging) for detecting cancer cells in a subject;
(b) a compound of formula I (or II), fluorescent nanodots or a pharmaceutical composition as described hereinbefore for use in the preparation of an in vivo imaging agent for detecting cancer cells in a subject;
(c) a method for detecting cancer cells in a subject comprising administering an effective amount of a compound of formula I (or II), fluorescent nanodots or a pharmaceutical composition as described hereinbefore, and imaging the subject with a molecular imaging device to detect the compound or composition in the subject.

In the above uses:
(a) the compound, nanodots or composition may specifically accumulate in cancer cells relative to non-cancer cells; and/or
(b) detection of the compound, nanodots or composition in an organ of the subject may be an indication that cancers cells are present in the organ; and/or
(c) the cancer cells may be lung cancer, breast cancer, prostate cancer, cervical cancer, pancreatic cancer, colon cancer, ovarian cancer, stomach cancer, esophagus cancer, skin cancer, heart cancer, liver cancer, bronchial cancer, testicular cancer, kidney cancer, bladder cancer, spleen cancer, thymus cancer, thyroid cancer, brain cancer, or gall bladder cancer cells; and/or
(d) the compound, nanodots or composition may be detected using an optical imaging device.

Compounds of formula I (or II) may be prepared in accordance with techniques that are well known to those skilled in the art, for example as described hereinafter (e.g. in the examples section hereinbelow).

In certain embodiments, the compounds of the present disclosure may be isolated from their reaction mixtures using conventional techniques (e.g. recrystallisation, column chromatography, preparative HPLC, etc.).

In the processes described above and hereinafter, the functional groups of intermediate compounds may need to be protected by protecting groups. Protecting groups may be removed in accordance with techniques that are well known to those skilled in the art and as described hereinafter. For example, protected compounds/intermediates described herein may be converted chemically to unprotected compounds using standard deprotection techniques.

The type of chemistry involved will dictate the need, and type, of protecting groups as well as the sequence for accomplishing the synthesis.

The use of protecting groups is fully described in "*Protective Groups in Organic Chemistry*", edited by J W F McOmie, Plenum Press (1973), and "*Protective Groups in Organic Synthesis*", 3rd edition, T. W. Greene & P. G. M. Wutz, Wiley-Interscience (1999).

As used herein, the term "functional groups" means, in the case of unprotected functional groups, hydroxy-, thiol-, aminofunction, carboxylic acid and, in the case of protected functional groups, lower alkoxy, N-, O-, S-acetyl, carboxylic acid ester.

Some advantages of the current application that arise from the compounds of formula I are described below.

| Feature | Benefit/Advantage |
| --- | --- |
| A molecular design strategy to produce far-red excitable near infrared fluorescent molecules with aggregation-induced emission (AIE) characteristics. | 1. The absorption profiles can be controlled by choosing appropriate acceptor units.<br>2. The emission maxima of the obtained chromophores can be tuned by changing the number of the substituted chains.<br>3. The AIE properties can be modulated by simply changing the position and length of substituted chain on peripheral TPE blocks. |
| NIR fluorescence imaging using the AIE-dots based on these obtained chromophores can be applied to accurate tumor detection and resection. | 1. Far-red excitable near infrared fluorescent AIE-dots.<br>2. High brightness and excellent biocompatibility.<br>3. High tumor-to-normal tissue ratio value and accurate tumor identification ability. |

The AIE-dots described herein are promising fluorescent agents for in vivo applications. Compared to FDA approved organic dye, indocyanine green (ICG), the quantum dots of the present disclosure solve two problems, namely photostability of traditional fluorophores, and quenching of fluorescence caused by aggregation.

Methods

Synthetic Route

Figure 2:
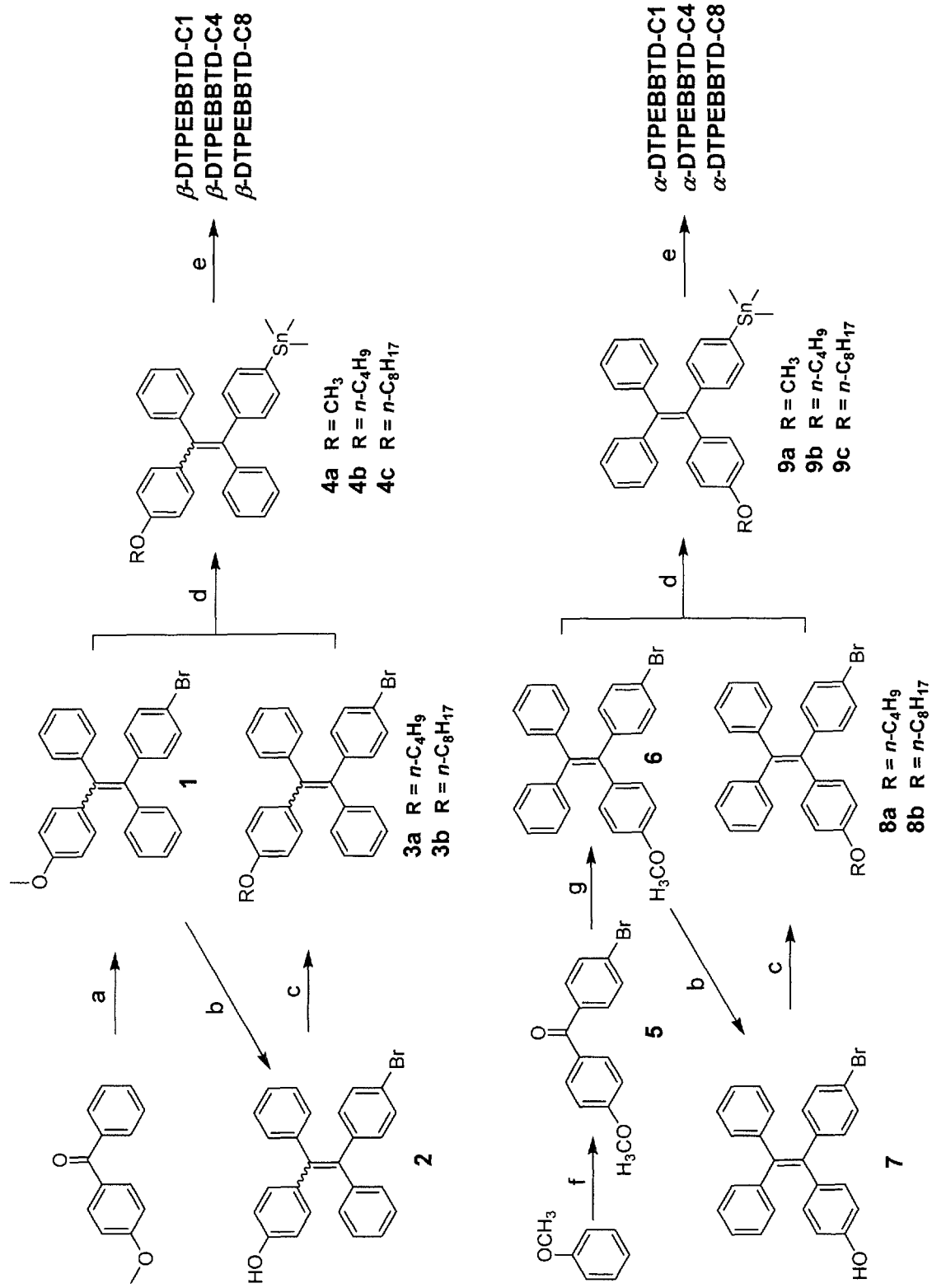

The synthetic route towards α-DTPEBBTD-Cx and β-DTPEBBTD-Cx, where x represents the number of carbons in the alkoxy chains, is outlined in FIG. 2. Briefly, the key steps to α-DTPEBBTD-Cx and β-DTPEBBTD-Cx are the Stille-coupling reaction of BBTD (step e in FIG. 2) with the corresponding trimethyltin compounds derived from monoalkoxy-substituted TPEs, which were synthesized by cross-coupling McMurry reaction using step (a) or alkoxylation of hydroxyl-functionalized TPEs using step (c). The NMR and MS data confirmed the correct chemical structure for each of the compounds depicted in FIG. 2. The obtained compounds show good solubility in common organic solvents due to the presence of alkoxy chains. Altogether, six AIE-molecules were synthesized, consisting of three α-DTPEBBTD-Cx molecules and three β-DTPEBBTD-Cx molecules, where x is 1, 4 or 8 and represents the number of carbon atoms in the alkoxy group.

Synthetic protocols for the intermediates 1-2, 3a-3b, 4a-c, 5-7, 8a-b, 9a-c and the six AIE molecules as shown in FIG. 2 are provided below.

1-(4-Bromophenyl)-2-(4-methoxyphenyl)-1,2-diphenylethene (1)

A two-necked round-bottom flask with a reflux condenser was charged with 4-bromobenzophenone (3.91 g, 15.0 mmol), 4-methoxybenzophenone (3.18 g, 15.0 mmol) and zinc (5.20 g, 80.0 mmol). The flask was degassed with three freeze-pump-thaw cycles to remove air, and then anhydrous THF (150 mL) was added. The mixture was cooled to −78° C. and $TiCl_4$ (4.9 mL, 45.0 mmol) was added dropwise by a syringe. The reaction mixture was slowly warmed to room temperature and stirred for 0.5 hour before it was heated to 80° C. for 24 hours. After cooling down to room temperature, the reaction was quenched by the addition of 10% $K_2CO_3$ aqueous solution (100 mL). The mixture was filtered to remove insoluble materials and washed with dichloromethane (150 mL). The organic layer was dried over $MgSO_4$ and filtered. After solvent removal, the residue was further purified by silica gel column chromatography (hexane/dichloromethane/ethyl acetate=8/2/0.1) to give compound 1 as a light green solid (3.79 g, yield: 57%). $^1$H NMR (400 MHz, $CDCl_3$, ppm): δ 7.15-7.38 (m, 2H), 7.33-7.28 (m, 2H), 7.16-7.10 (m, 4H), 7.06-7.01 (m, 4H), 6.99-6.91 (m, 4H), 6.74-6.67 (m, 2H), 3.73 (d, 3H). $^{13}$C NMR (100 MHz, $CDCl_3$, ppm): δ 158.3, 143.6, 143.0, 141.2, 135.6, 133.0, 132.5, 132.4, 131.4, 131.3, 130.9, 130.8, 130.1, 128.4, 128.3, 127.8, 127.7, 127.6, 126.5, 126.4, 120.2, 113.0, 55.6, 55.0.

1-(4-Bromophenyl)-2-(4-hydroxyphenyl)-1,2-diphenylethene (2)

To a solution of compound 1 (3.53 g, 8.0 mmol) in anhydrous dichloromethane (20 mL) under an argon atmosphere, was slowly added boron tribromide solution (1 M in dichloromethane, 10.5 mL, 10.5 mmol) at −78° C. Then the reaction mixture was stirred at room temperature overnight. After quenching with ice water, the crude product was sequentially extracted with dichloromethane (50 mL×3), washed with water (100 mL×3), dried over $Na_2SO_4$ and filtered. After solvent removal, the residue was purified by silica gel column chromatography (hexane/dichloromethane=3/7) to afford compound 2 as a light green solid (3.13 g, yield: 92%). $^1$H NMR (400 MHz, $CDCl_3$, ppm): δ 7.25-7.19 (m, 2H), 7.14-6.98 (m, 10H), 6.92-6.86 (m, 4H), 6.60-6.55 (m, 2H), 4.88 (d, 1H). $^{13}$C NMR (100 MHz, $CDCl_3$, ppm): δ 153.66, 153.55, 142.93, 142.88, 142.85, 142.35, 142.26, 140.47, 138.24, 138.20, 135.38, 135.27, 132.36, 132.06, 132.04, 130.64, 130.27, 130.17, 127.22, 127.11, 127.02, 126.04, 125.94, 125.87, 119.63, 114.18, 113.99.

1-(4-Bromophenyl)-2-(4-butoxyphenyl)-1,2-diphenylethene (3a)

To a mixture of compound 2 (852.0 mg, 2.0 mmol) and cesium carbonate ($Cs_2CO_3$, 975.0 mg, 3.0 mmol) in anhydrous dimethylformamide (DMF, 5.0 mL), 1-bromobutane (0.32 mL, 3.0 mmol) was added under argon atmosphere. The reaction mixture was stirred at room temperature overnight. After quenching with water, the crude product was sequentially extracted with dichloromethane (30 mL×3), washed with water (50 mL×3), and dried over $MgSO_4$. After solvent removal, the residue was further purified by silica gel column chromatography (hexane/dichloromethane=9/1) to give the compound 3a as a light green fibrous solid (927 mg, yield: 96%). $^1$H NMR (400 MHz, $CDCl_3$, ppm): δ 7.28-7.21 (m, 2H), 7.14-7.01 (m, 10H), 6.95-6.87 (m, 4H), 6.69-6.64 (m, 2H), 3.93-3.88 (m, 2H), 1.79-1.73 (m, 2H), 1.54-1.47 (m, 2H), 1.01-0.97 (m, 3H). $^{13}$C NMR (100 MHz, $CDCl_3$, ppm): δ 157.90, 157.80, 143.67, 143.60, 143.56, 143.47, 143.04, 142.98, 141.26, 138.63, 138.58, 135.39, 132.98, 132.43, 132.41, 132.38, 131.30, 131.27, 131.02, 130.91, 130.86, 130.75, 127.81, 127.70, 127.58, 126.48, 126.41, 120.45, 120.18, 113.78, 113.74, 113.57, 67.48, 67.44, 31.34, 31.32, 19.24, 13.89, 13.87.

1-(4-Bromophenyl)-2-(4-octyloxyphenyl)-1,2-diphenylethene (3b)

The compound 3b was synthesized with similar synthetic procedure of compound 3a, starting from compound 2 (852.0 mg, 2 mmol), $Cs_2CO_3$ (975.0 mg, 3 mmol), DMF (5.0 mL) and 1-bromooctane (0.52 mL, 3 mmol). The crude product was purified by silica gel column chromatography (hexane/dichloromethane=9/1) to give the compound 3b as a light green fibrous solid (1.0 g, yield: 93%). δ 7.28-7.24 (m, 2H), 7.17-7.04 (m, 10H), 6.98-6.91 (m, 4H), 6.71-6.66 (m, 2H), 3.95-3.90 (m, 2H), 1.82-1.75 (m, 2H), 1.48-1.44 (m, 2H), 1.36-1.33 (m, 8H), 0.95-0.93 (m, 3H). $^{13}$C NMR (100 MHz, $CDCl_3$, ppm): δ 157.92, 157.83, 143.70, 143.63, 143.59, 143.50, 143.01, 141.28, 138.62, 135.53, 133.02, 132.49, 132.46, 132.43, 131.39, 131.33, 131.30, 130.89, 130.78, 127.84, 127.80, 127.72, 127.69, 127.61, 127.57, 126.61, 126.51, 126.43, 120.19, 113.77, 113.60, 67.91, 67.82, 31.82, 29.40, 29.38, 29.31, 29.30, 29.24, 29.23, 26.08, 26.07, 22.66, 14.12.

1,2-Diphenyl-2-(4-methoxyphenyl)-1-(4-trimethylstannylphenyl)ethene (4a)

To a solution of compound 1 (441.0 mg, 1.0 mmol) in anhydrous THF (10 mL) at −78° C. under argon atmosphere, n-BuLi (1.6 M in hexane, 0.93 mL, 1.5 mmol) was slowly added. After the reaction mixture was stirred at −78° C. for 1.5 hours, trimethyltin chloride ($Me_3SnCl$, 1.0 M in THF, 1.8 mL) was added to the mixture in one portion. Then it was slowly warmed to room temperature and stirred overnight. The mixture was poured into water and extracted with dichloromethane (30 mL×3). The combined organic layer was sequentially washed with water (100 mL×3), dried over $Na_2SO_4$, and filtered. After removal of the solvent, the residue was obtained as a colorless liquid and directly used in the next step without further purification.

2-(4-Butoxyphenyl)-1,2-diphenyl-1-(4-trimethyl-stannylphenyl)ethene (4b)

Compound 4b was synthesized by a synthetic procedure similar to that of compound 4a, starting from compound 3a (483.0 mg, 1.0 mmol), n-BuLi (1.6 M in hexane, 0.93 mL, 1.5 mmol), $Me_3SnCl$ (1.0 M in THF, 1.8 mL) and anhydrous THF (15 mL). The obtained colorless liquid was used directly in the next step without further purification.

1,2-Diphenyl-2-(4-octyloxyphenyl)-1-(4-trimethyl-stannylphenyl)ethene (4c)

Compound 4c was synthesized with a synthetic procedure similar to that of compound 4a, starting from compound 3b (539.0 mg, 1.0 mmol), n-BuLi (1.6 M in hexane, 0.93 mL, 1.5 mmol), $Me_3SnCl$ (1.0 M in THF, 1.8 mL) and anhydrous THF (15 mL). The obtained colorless liquid was used directly in the next step without further purification.

β-DTPEBBTD-C$_1$.

A solution of compound 4a (210.0 mg, 0.4 mmol), 4,8-dibromobenzo[1,2-c:4,5-c']bis([1,2,5]thiadiazole) (dibromoBBTD, 35.2 mg, 0.1 mmol) and $Pd(PPh_3)_4$. (11.5 mg, 10 μmol) in toluene (30 mL) were heated at 100° C. under argon atmosphere for 36 hours. After cooling to room temperature, the mixture was sequentially diluted with dichloromethane (200 mL), washed with water (200 mL×3) and dried over $MgSO_4$. After solvent removal, the residue was purified by silica gel column chromatography (hexane/dichloromethane=4/6) to afford β-DTPEBBTD-C1 as a blue solid (38.4 mg, yield: 42%). $^1$H NMR (400 MHz, CDCl$_3$, ppm) δ 8.09-8.03 (m, 4H), 7.33-7.29 (m, 4H), 7.16-6.98 (m, 24H), 6.73-6.66 (m, 4H), 3.76 (s, 0.86), 3.73 (s, 5.14). $^{13}$C NMR (100 MHz, CDCl$_3$, ppm) δ 158.52, 152.87, 144.77, 144.16, 144.02, 141.63, 139.84, 136.18, 133.16, 132.80, 131.74, 131.58, 131.45, 131.40, 127.98, 127.86, 127.74, 126.60, 126.52, 121.03, 113.46, 55.25.

β-DTPEBBTD-C4.

Compound β-DTPEBBTD-C4 was obtained as a blue solid (50.8 mg, yield: 51%) using a similar synthetic procedure to that set out above for compound ρ-DTPEBBTD-C1, starting from compound 4b (226.8 mg, 0.4 mmol), dibromoBBTD (35.2 mg, 0.1 mmol), $Pd(PPh_3)_4$ (11.5 mg, 10 μmol) and toluene (30 mL). $^1$H NMR (400 MHz, CDCl$_3$, ppm) δ 8.10-8.02 (m, 4H), 7.34-7.27 (m, 4H), 7.23-7.09 (m, 22H), 7.00-6.98 (d, J=8 Hz, 2H), 6.73-6.66 (m, 4H), 3.93-3.88 (m, 4H), 1.77-1.70 (m, 4H), 1.52-1.44 (m, 4H), 1.01-0.92 (m, 6H). $^{13}$C NMR (100 MHz, CDCl$_3$, ppm) δ 158.11, 157.93, 152.83, 152.80, 152.77, 144.81, 144.80, 144.73, 144.20, 144.14, 144.07, 144.06, 141.70, 139.70, 136.06, 135.93, 133.10, 133.07, 132.77, 132.72, 131.74, 131.71, 131.64, 131.59, 131.43, 131.40, 131.33, 127.95, 127.84, 127.70, 126.76, 127.57, 126.48, 120.99, 120.95, 120.92, 113.98, 113.72, 67.63, 31.50, 31.46, 19.38, 19.36, 14.00, 13.98.

β-DTPEBBTD-C8.

Compound β-DTPEBBTD-C8 was obtained as a blue solid (59.9 mg, yield: 54%) using a similar synthetic procedure to that used for compound β-DTPEBBTD-C1, starting from compound 4c (249.2 mg, 0.4 mmol), dibromoBBTD (35.2 mg, 0.1 mmol), $Pd(PPh_3)_4$ (11.5 mg, 10 μmol) and toluene (30 mL). $^1$H NMR (400 MHz, CDCl$_3$, ppm) δ 8.10-8.02 (m, 4H), 7.33-7.27 (m, 4H), 7.21-7.08 (m, 22H), 6.99-6.97 (d, J=8 Hz, 2H), 6.72-6.65 (m, 4H), 3.92-3.86 (m, 4H), 1.78-1.71 (m, 4H), 1.33-1.26 (m, 20H), 0.93-0.85 (m, 6H). $^{13}$C NMR (100 MHz, CDCl$_3$, ppm) δ 158.12, 157.94, 152.88, 152.85, 152.83, 144.83, 144.79, 144.76, 144.75, 144.22, 144.16, 144.08, 141.72, 139.71, 136.07, 135.94, 133.13, 133.10, 132.78, 132.73, 131.76, 131.73, 131.66, 131.61, 131.43, 131.33, 127.97, 127.96, 127.85, 127.71, 126.76, 126.58, 126.49, 121.06, 121.03, 120.99, 113.99, 113.74, 67.99, 31.95, 31.90, 29.52, 29.48, 29.45, 29.43, 29.36, 29.32, 26.19, 22.79, 22.75, 14.24, 14.20.

(4-Bromophenyl)(4-methoxyphenyl)methanone (5).

To a solution of 4-bromobenzoyl chloride (2.17 g, 10.0 mmol) and aluminum chloride (1.36 g, 10.2 mmol) in dry dichloromethane (15 mL) under argon atmosphere in ice bath, anisole (3.26 mL, 30 mmol) was added. The mixture was kept at 0-10° C. for 1 hour and then stirred at room temperature overnight. Hydrochloric acid aqueous solution (100 mL, 1 M) was carefully added into the reaction mixture in ice bath to afford great precipitates. After filtration under reduced pressure, the obtained solid was further purified by silica gel column chromatography using a mixture of hexane/ethyl acetate (9/1) as eluent to give (4-bromophenyl)(4-methoxyphenyl)methanone as a white solid. $^1$H NMR (400 MHz, CDCl$_3$, ppm) δ 7.81-7.78 (m, 2H), 7.65-7.62 (m, 4H), 6.98-6.95 (m, 2H), 3.89 (s, 3H).

1-(4-Bromophenyl)-2,2-diphenyl-1-(4-methoxyphenyl) ethene (6).

Diphenylmethane (2.02 g, 12.0 mmol) in anhydrous THF (50 mL) was stirred at 0° C. under argon atmosphere, then n-BuLi (1.6 M in hexane, 6.87 mL, 11.0 mmol) was added into the mixture dropwise. The resultant red mixture was kept at 0° C. for 1 hour, then a solution of compound 5 (2.91 g, 10 mmol) in anhydrous THF (10 mL) was added slowly. The reaction mixture was stirred at room temperature overnight. After treatment with a saturated NH$_4$Cl aqueous solution, the crude product was extracted with dichloromethane (50 mL×3). The combined organic phase was sequentially washed with water, dried over MgSO$_4$ and filtered to remove the MgSO$_4$. After solvent removal, the residue and p-toluenesulfonic acid (86.0 mg, 0.5 mmol) were treated in toluene (25 mL) at 100° C. for 3 hours. The crude product was sequentially extracted with dichloromethane (50 mL×3), washed with water (100 mL×3), and dried over MgSO$_4$. After solvent removal, the residue was purified by silica gel column chromatography (hexane/dichloromethane/ethyl acetate=8/2/0.2) to yield compound 6 as a white solid (3.48 g, yield: 79%). $^1$H NMR (400 MHz, CDCl$_3$, ppm) δ 7.23-7.22 (m, 2H), 7.14-7.10 (m, 6H), 7.04-7.01 (m, 4H), 6.93-6.90 (m, 4H), 6.66-6.64 (m, 2H), 3.75 (s, 3H). $^{13}$C NMR (100 MHz, CDCl$_3$, ppm) δ 158.38, 143.86, 143.71, 143.11, 140.85, 139.37, 135.71, 133.17, 132.64, 131.41, 131.36, 130.93, 127.97, 127.88, 126.65, 126.56, 120.49, 113.31, 55.24.

2,2-Diphenyl-1-(4-bromophenyl)-1-(4-hydroxyphenyl) ethene (7).

Compound 7 was obtained as a light green solid (2.0 g, yield: 91%) using a procedure similar to that used to obtain compound 2, starting from compound 6 (2.2 g, 5.0 mmol) and BBr$_3$ solution (1 M in dichloromethane, 7 mL, 7.0 mmol). $^1$H NMR (400 MHz, CDCl$_3$, ppm) δ 7.23-7.20 (m, 2H), 7.13-7.09 (m, 6H), 7.02-6.99 (m, 4H), 6.59-6.55 (m, 2H), 4.58 (s, 1H). $^{13}$C NMR (100 MHz, CDCl$_3$, ppm) δ 154.42, 143.83, 143.64, 143.00, 140.90, 139.32, 135.84, 133.14, 132.82, 131.38, 131.33, 130.93, 127.96, 127.87, 126.67, 126.56, 120.51, 114.88.

2,2-Diphenyl-1-(4-bromophenyl)-1-(4-butoxyphenyl) ethene (8a).

Compound 8a was obtained as a fibrous solid (888.6 mg, yield: 92%) using similar synthetic procedure to that used for obtaining compound 3a, starting from compound 7 (854.0 mg, 2.0 mmol), $Cs_2CO_3$ (975.0 mg, 3.0 mmol), DMF (5.0 mL) and 1-bromobutane (0.32 mL, 3.0 mmol). $^1$H NMR (400 MHz, $CDCl_3$, ppm) δ 7.25-7.23 (m, 2H), 7.14-7.10 (m, 6H), 7.06-7.01 (m, 4H), 6.94-6.90 (m, 4H), 6.67-6.62 (m, 2H), 3.91 (t, J=8 Hz, 2H), 1.76 (m, 2H), 1.50 (m, 2H), 0.98 (t, J=8 Hz, 3H). $^{13}$C NMR (100 MHz, $CDCl_3$, ppm) δ 158.00, 143.90, 143.76, 143.15, 140.72, 139.45, 135.46, 133.20, 132.61, 131.42, 131.36, 130.91, 127.96, 127.87, 126.62, 126.52, 120.47, 113.83, 67.64, 31.49, 19.40, 14.04.

2,2-Diphenyl-1-(4-octyloxyphenyl)-1-(4-bromophenyl) ethene (8b).

Compound 8b was obtained as a viscous oil (948.6 mg, yield: 88%) using similar synthetic procedure to that used for obtaining compound 3b, starting from compound 7 (854.0 mg, 2.0 mmol), $Cs_2CO_3$ (975.0 mg, 3.0 mmol), DMF (5.0 mL) and 1-bromooctane (0.52 mL, 3 mmol). $^1$H NMR (400 MHz, $CDCl_3$, ppm) δ 7.24-7.20 (m, 2H), 7.14-7.10 (m, 6H), 7.05-7.00 (m, 4H), 6.92-6.89 (m, 4H), 6.66-6.62 (m, 2H), 3.88 (t, J=8 Hz, 2H), 1.75 (m, 2H), 1.44 (m, 2H), 1.36-1.30 (m, 8H), 0.90 (t, J=8 Hz, 3H). $^{13}$C NMR (100 MHz, $CDCl_3$, ppm) δ 158.04, 143.93, 143.79, 143.18, 140.76, 139.50, 135.49, 133.20, 132.62, 131.43, 131.37, 130.92, 127.97, 127.88, 126.63, 126.53, 120.48, 113.88, 68.02, 31.96, 29.52, 29.44, 29.36, 26.20, 22.80, 14.23.

Compounds 9a-c.

Compounds 9a-c were synthesized with similar procedures to corresponding compounds 4a-c, and used directly without further purification.

α-DTPEBBTD-C1.

Compound α-DTPEBBTD-C1 was synthesized according to the synthetic procedure used to synthesize compound β-DTPEBBTD-C1, starting from compound 9a (210.0 mg, 0.4 mmol), dibromoBBTD (35.2 mg, 0.1 mmol), $Pd(PPh_3)_4$ (11.5 mg, 10 μmol) and toluene (30 mL). Due to the poor solubility of α-DTPEBBTD-C1 in the NMR solvent, $^{13}$C NMR spectrum for α-DTPEBBTD-C1 was not obtained. $^1$H NMR (400 MHz, $CDCl_3$, ppm) ti 8.07 (d, J=8 Hz, 4H), 7.30 (d, J=8 Hz, 4H), 7.15-7.05 (m, 24H), 6.68 (d, J=8 Hz, 4H), 3.76 (s, 6H).

α-DTPEBBTD-C4.

Compound α-DTPEBBTD-C4 was synthesized according to the synthetic procedure used to synthesize compound β-DTPEBBTD-C1, starting from compound 9b (226.8 mg, 0.4 mmol), dibromoBBTD (35.2 mg, 0.1 mmol), $Pd(PPh_3)_4$ (11.5 mg, 10 μmol) and toluene (30 mL). $^1$H NMR (400 MHz, $CDCl_3$, ppm) δ 8.06 (d, J=8 Hz, 4H), 7.30 (d, J=8 Hz, 4H), 7.16-7.08 (m, 20H), 7.06 (d, J=8 Hz, 4H), 6.69 (d, J=8 Hz, 4H), 3.91 (t, J=8 Hz, 4H), 1.74 (t, J=8 Hz, 4H), 1.50-1.44 (m, 4H), 0.97 (t, J=8 Hz, 6H). $^{13}$C NMR (100 MHz, $CDCl_3$, ppm) δ 158.01, 152.91, 144.80, 144.29, 144.08, 141.11, 140.39, 135.96, 133.28, 132.90, 131.63, 131.56, 131.51, 131.32, 127.97, 127.85, 126.64, 126.46, 121.11, 113.88, 67.69, 31.54, 19.41, 14.02.

α-DTPEBBTD-C8.

Compound α-DTPEBBTD-C8 was synthesized according to the synthetic procedure used to synthesize compound β-DTPEBBTD-C1, starting from compound 9c (249.2 mg, 0.4 mmol), dibromoBBTD (35.2 mg, 0.1 mmol), $Pd(PPh_3)_4$ (11.5 mg, 10 μmol) and toluene (30 mL). $^1$H NMR (400 MHz, $CDCl_3$, ppm) δ 8.06 (d, J=8 Hz, 4H), 7.30 (d, J=8 Hz, 4H), 7.15-7.08 (m, 20H), 7.05 (d, J=8 Hz, 4H), 6.68 (d, J=8 Hz, 4H), 3.89 (t, J=8 Hz, 4H), 1.78-1.71 (m, 4H), 1.44 (m, 4H), 1.33-1.28 (m, 16H), 0.89 (t, J=8 Hz, 6H). $^{13}$C NMR (100 MHz, $CDCl_3$, ppm) δ 158.01, 152.92, 144.81, 144.30, 144.09, 141.11, 140.40, 135.96, 133.28, 132.90, 131.63, 131.56, 131.51, 131.33, 127.97, 127.85, 126.64, 126.46, 121.12, 113.90, 68.04, 31.96, 29.53, 29.48, 29.37, 26.22, 22.80, 14.23.

Figure 3:
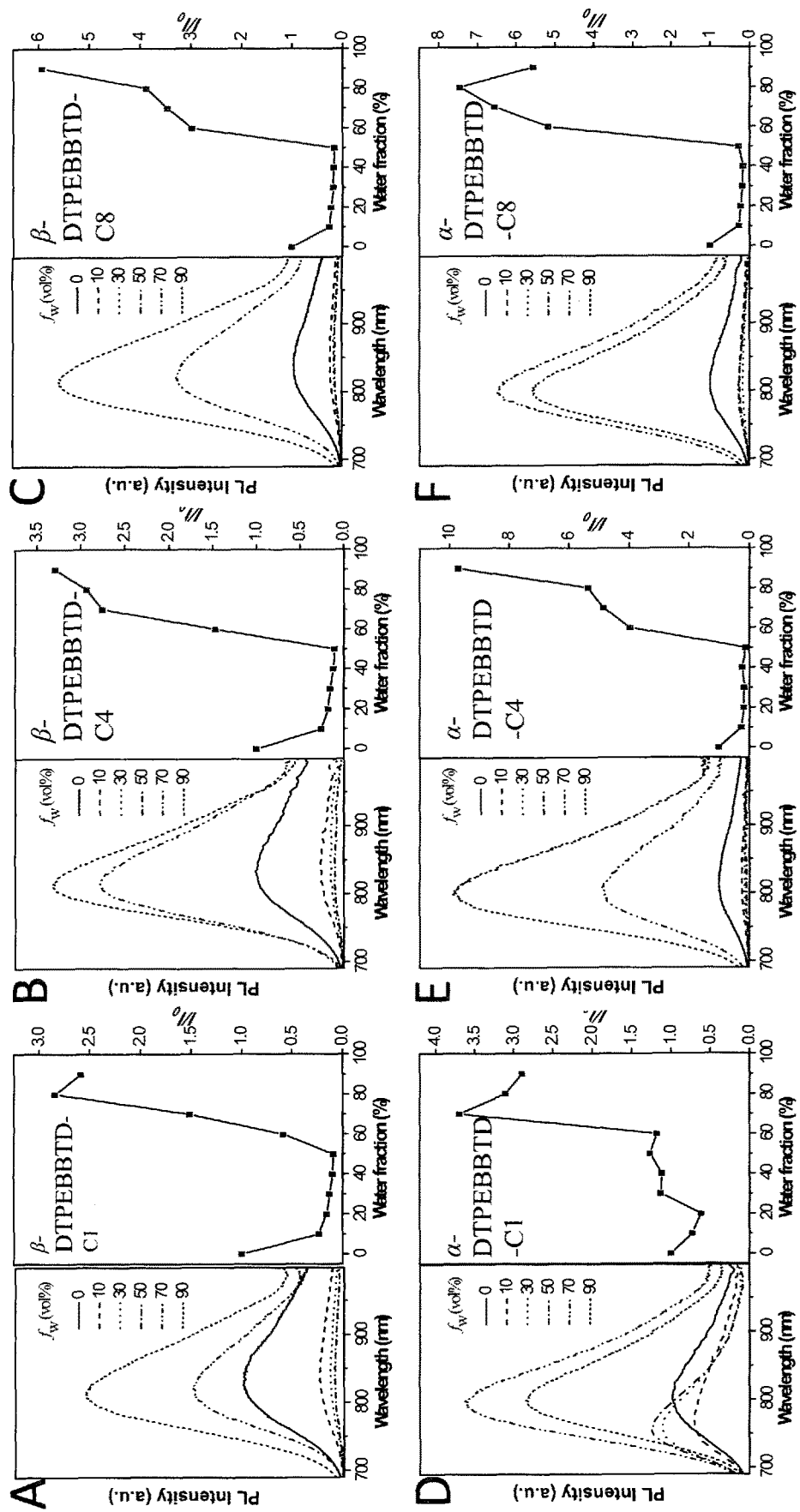

Example 1: Change in Photoluminescence (PL) Intensity of Compounds in THF when Titrated with Water The AIE properties of α-DTPEBBTD-Cx and β-DTPEBBTD-Cx were verified by studying their photoluminescence (PL) spectra in a mixture of THF/water with varying water fractions ($f_w$), which enabled fine-tuning of the solvent polarity and the extent of solute aggregation. Specifically for α-DTPEBBTD-C4, it exhibits weak NIR fluorescence in pure THF solution with an emission peak at 814 nm (FIG. 3E). Its fluorescence intensity is further weakened by gradually addition of water in the THF (fw≤50 vol %), accompanied with bathochromic shift from 814 nm to 836 nm, presumably due to the twisted intramolecular charge transfer (TICT) state caused by the increased polarity. The presence of ICT in these molecules was also confirmed by the solvent-dependent emission and calculated frontier orbitals. Such a TICT phenomenon is very common phenomenon for donor-acceptor (D-A) structured molecules that featured with red shifted emission and decreased emission intensity with increasing solvent polarity. As the water fraction exceeds 50 vol %, α-DTPEBBTD-C4 undergoes a transition from solute to aggregates, and the fluorescence intensity dramatically increases. As revealed in the inset of FIG. 1E, α-DTPEBBTD-C4 shows ~10-fold higher fluorescence intensity in aggregates than that in pure THF, indicative of AIE characteristics. In addition, without wishing to be bound by theory, it is believed that when the molecules aggregate, the local environment becomes less polar and the D-A structure becomes less twisted. Thus, a hypochromatic shift from 836 to 804 nm was observed for the emission maximum, owing to the TICT-to-local emission transition. Other compounds show similar AIE behavior except for α-DTPEBBTD-C1, which shows fluorescence enhancement when the water fraction is higher than 20%, because the aggregation occurs at such lower water content due to its poor solubility. Interestingly, the AIE titration results reveal that the extent of fluorescence enhancement is dependent upon the variation of the substitutions, suggesting that the position and length of substituted chain has great effect on its optical properties.

Example 2: Preparation and Characterization of AIE-Dots

Amphiphilic DSPE-$PEG_{2000}$ (1,2-Distearoyl-sn-Glycero-3-Phosphoethanolamine conjugated Polyethylene Glycol)

was employed as the matrix to formulate the six AIE compounds into nanodots (AIE-dots) through the nanoprecipitation approach outlined in FIG. 4A.

Fabrication of AIE-dots.

Each of the AIE molecules (α-DTPEBBTD-Cx and β-DTPEBBTD-Cx; where x represents 1, 4, and 8) (1 mg) and DSPE-PEG$_{2000}$ (2 mg) were dissolved in THF (1 mL) and then added into water (10 mL), followed by sonication for 2 min using a microtip sonicator at 16 W output (XL2000, Misonix Incorporated, NY). After the mixture was stirred vigorously for 24 hours to evaporate THF, the mixture was filtered using a 0.2 μm syringe driven filter to give the corresponding AIE-dots for further use.

Characterization.

The size and morphology of the AIE-dots were characterized by laser light scattering (LLS) and transmission electron microscopy (TEM). FIG. 4B gives the representative results, revealing that the AIE-dots have a sphere shape with a mean diameter of 46 nm, which is slightly smaller than that obtain from LLS (54 nm). The obtained AIE-dots can be stably stored at 4° C. over 3 months without any suspensions. The absorption spectra of these α-DTPEBBTD-Cx and β-DTPEBBTD-Cx based AIE-dots are shown in FIG. 4C. The absorption bands from 300 to 450 nm are assigned to the π-π* and n-π* transitions of the conjugated aromatic skeleton while those at lower energy bands peaked at 635 nm are attributed to the intramolecular charge transfer (ICT) from donor to acceptor units. It would be clear that the absorption spectra are almost identical, indicating that the variation of position and length of the substituted chains has little effect on the ground state of these molecules, which is also supported by the constant HOMO and LUMO levels. As shown in FIG. 4D, the emission spectra of all the AIE-dots are mainly located within 700-900 nm region, which is beneficial to in vivo NIR fluorescence imaging. Unlike the constant absorption profile, the PL spectra of the AIE-dots show three general trends. First, α-DTPEBBTD-Cx based AIE-dots have emission maxima at 801 nm while β-DTPEBBTD-Cx based AIE-dots at 815 nm. Second, the fluorescence intensity is gradually enhanced as longer substituted chains are employed. Third, α-DTPEBBTD-Cx based AIE-dots have stronger fluorescence than β-DTPEBBTD-Cx based ones. The spectral profile of these AIE-dots minimizes overlap with known regions of intense autofluorescence and they can be excited by readily available laser line at 635 nm, which would maximize its light-harvesting ability. Additionally, large Stokes shifts of 136 nm for α-DTPEBBTD-Cx and 150 nm for β-DTPEBBTD-Cx based AIE-dots would greatly minimize the self-absorption effect typically observed in conventional organic dyes and the interference between the absorption and emission signals.

The impact of chain lengths on optical properties is also reflected on the quantum yield (QY), which was determined using IR-125 in DMSO as a reference (13%). FIG. 4E shows that the QY of the AIE-dots goes up when longer substituent is used (from 3.8% to 4.8% for α-DTPEBBTD-Cx and from 2.2% to 3.8% for (3-DTPEBBTD-Cx based AIE-dots) and that the α-DTPEBBTD-Cx based AIE-dots have higher QYs than β-DTPEBBTD-Cx based ones. Without wishing to be bound by theory, it is believed that the intense NIR fluorescence observed for the AIE-dots can be attributed to AIE effect caused by the aggregates formation, in which the suppression of π-π stacking resulting from the substituted TPE blocks and the restriction of intramolecular rotations result in enhancement of fluorescence intensity. Additionally, preventing the molecules from contact with water by encapsulation should be also taken into account. Comparison with the optical properties of these AIE-dots provides strong support that changing the substitution on the peripheral TPE blocks is a facile but efficient way to improve their AIE properties, which would be a guidance for designing new NIR fluorescent molecules.

Example 3: Effect of Using Silica Nanoparticles and Polystyrene Spacer

As our AIE molecules have ICT character, which enables the fluorescence property of the fluorophores to be related to the polarity of the environments. That is, the more polar of the environment, the less fluorescent of the fluorophore. Therefore, we constructed AIE-loaded silica nanoparticles (AIE@silica NPs) to improve the quantum yield.

Fabrication of AIE@Silica or AIEPS@Silica Nanoparticles

Firstly, 100 mg of poloxamer 407 (Pluronic™ F127; from BASF) (100 mg) and 1 mg of AIE fluorogens (or AIE and polystyrene) were well dissolved in 3 mL of THF and stirred for 3 h at room temperature. The solvents were then removed under gentle nitrogen flow, yielding a solid residue. 1.6 mL of 0.85 M hydrochloride solution was subsequently added into the solid poloxamer/AIE (or poloxamer/AIE/PS) mixture under sonication to form a homogeneous suspension. Then, 180 μL of tetraethyl orthosilicate (TEOS) was added into the mixture and the solution was further stirred for 2 h at room temperature. 30 μL of diethoxydimethylsilane (DEDMS) was subsequently added to the mixture to terminate the silica shell growth at NP surfaces. The reaction mixture was stirred for another 24 h at room temperature. Finally, the solution was dialyzed with a membrane (cut-off MW=14 000) against Milli-Q water for three days to remove hydrochloride and unreacted reagents. The suspension was then purified using a 0.2 μm syringe filter to yield AIE@Silica or AIEPS@Silica NPs.

Characterization.

Figure 5:
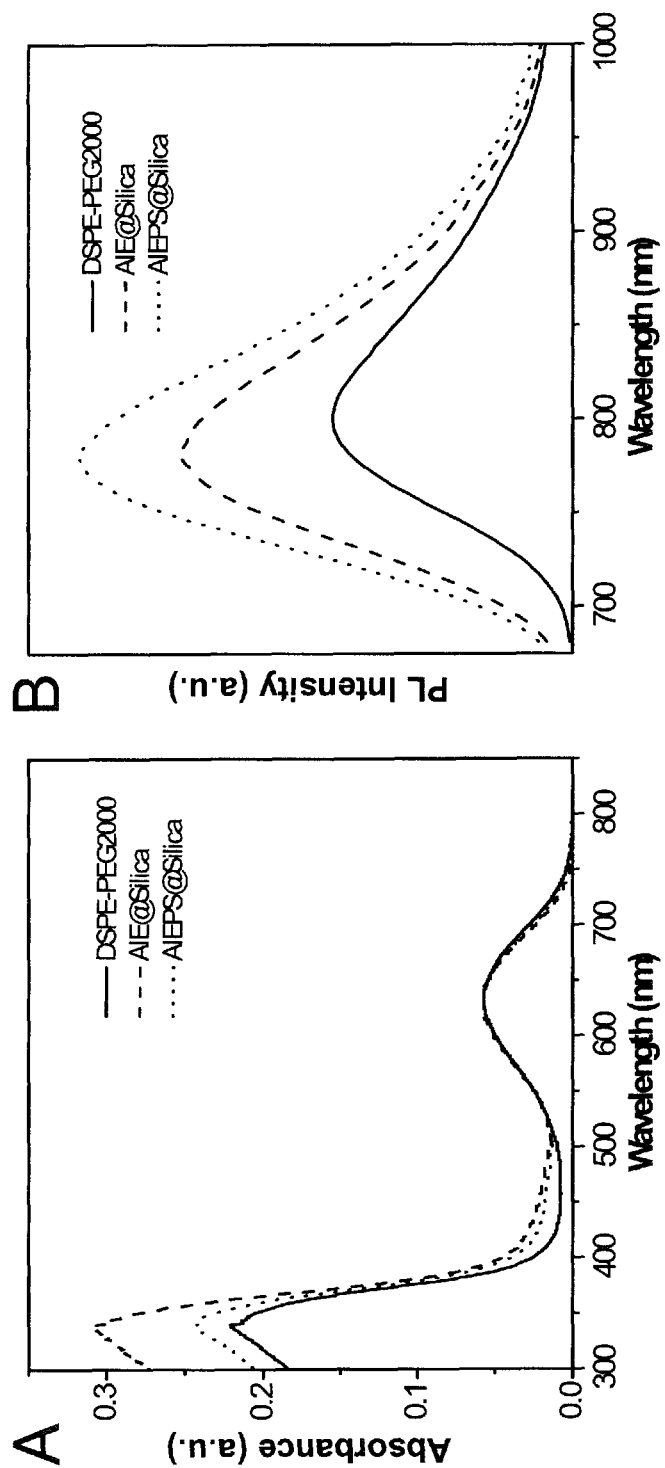
FIG. 5A depicts UV-vis and FIG. 5B depicts PL spectra of DSPE-PEG$_{2000}$, AIE@silica and AIEPS@silica NPs in water.

As shown in FIG. 5A, the UV-vis absorption spectra have two absorption peaks, which is similar to the DSPE-PEG$_{2000}$ formulated AIE-dots. The relatively higher intensity from 300-450 nm is due to light scattering. The PL spectra of the AIE@silica NPs exhibit blueshifts to 780 nm compared to AIE-dots, indicating the silica shell can provide a relatively hydrophobic microenvironment. The quantum yield of the AIE@silica was enhanced to 8%. As π-π stacking is associated with the fluorescent properties of conjugated molecules, reducing the intermolecular interaction would be good strategy. To confirm this idea, we used polystyrene as a spacer to separate the AIE molecules when they are in aggregated state. As shown in FIG. 5B, the fluorescence of AIE-loaded with Polystyrene spacer silica nanoparticles (AIEPS@silica NPs) is further enhanced with quantum yield of 9.5% compared to AIE@silica NPs.

Example 4: Application of AIE-Dots in Cell Imaging

Figure 6:
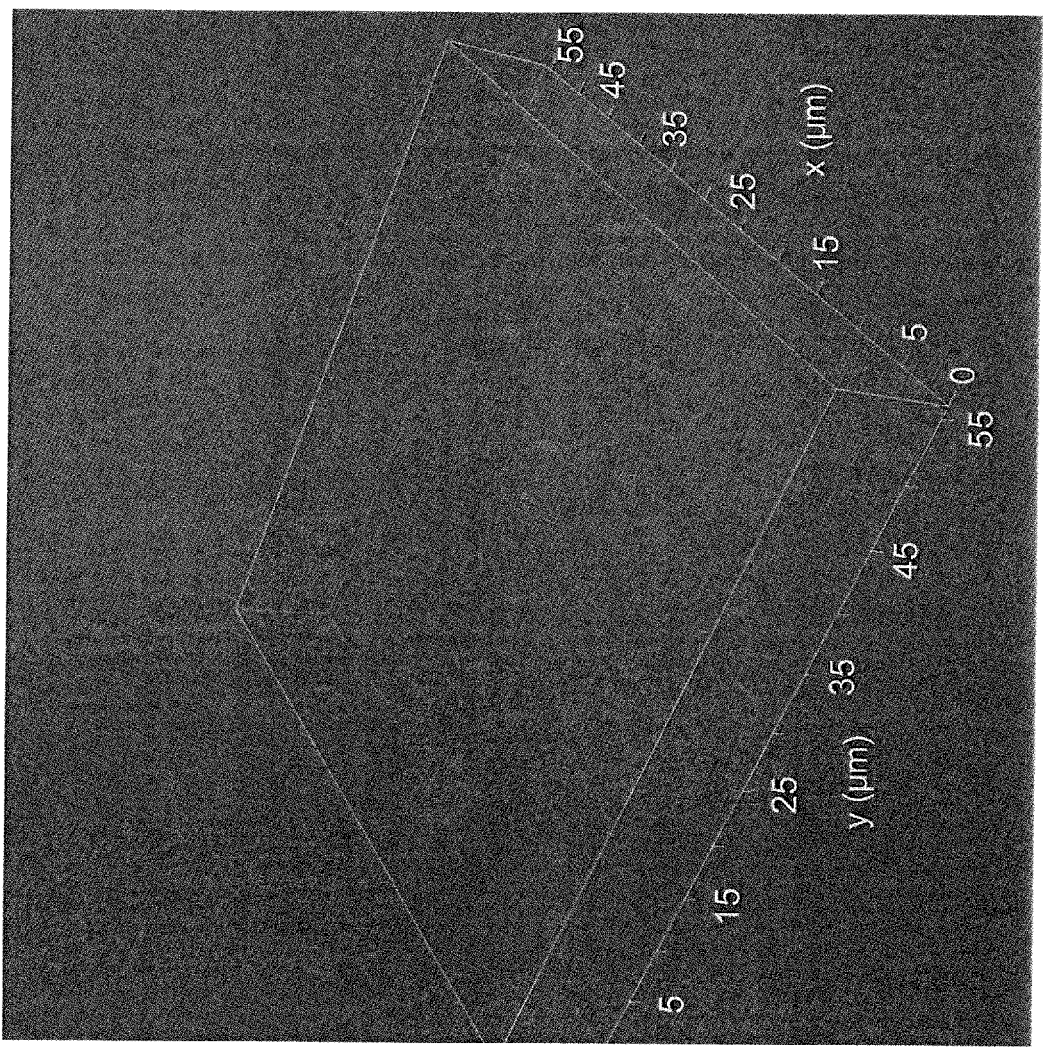
FIG. 6 depicts a 3D confocal image of 4T1 breast cancer cells after incubation with AIE-dots (2 nM) for 2 hours at 37° C.

The promising optical properties of these AIE-dots motivated us to further study their biological applications. 4T1 breast cancer cells were incubated with AIE-dots (2 nM) for 2 hours at 37° C. They were visualized with confocal microscopy with laser excitation at 633 m. The cell imaging results demonstrates that these AIE-dots can be used for high-contrast cell imaging upon laser excitation at 633 nm equipped by confocal microscopy due to its high NIR fluorescence (FIG. 6).

Cell Culture.

Luciferase-expressed 4T1 breast cancer cells and L02 hepatic cells were cultured in Dulbecco's Modified Eagle's Medium (DMEM) containing 10% FBS and 1% penicillin-streptomycin at 37° C. in a humidified environment containing 5% $CO_2$, respectively. Before experiments, the cells were precultured until confluence was reached.

Cell Imaging.

4T1 cancer cells were cultured in confocal imaging chambers at 37° C. AIE-dots (2 nM) in FBS-free culture medium were added to the chamber. After incubation for 2 h, the cells were washed with 1×PBS buffer and then fixed with 4% paraformaldehyde. After stained by DAPI for 10 min, the cells were imaged by confocal laser scanning microscope (Zeiss LSM 410, Jena, Germany). The fluorescent signal from AIE-dots was collected from 700 to 800 nm upon excitation at 633 nm.

Example 5: Toxicity Study of AIE-Dots Against Cancer and Normal Cells

Figure 7:
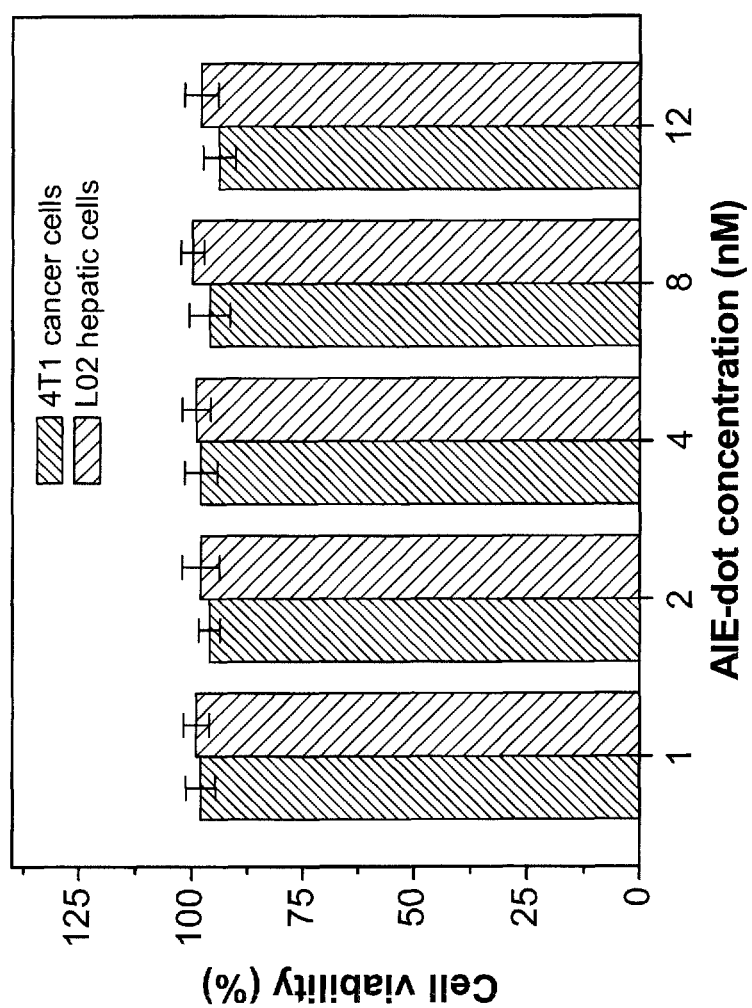
FIG. 7 depicts cell viabilities of 4T1 cancer cells and L02 hepatic cells (normal cells) after incubation with α-DT-PEBBTD based AIE-dots at different concentrations for 48 hours, respectively.

4T1 cancer cells and L02 hepatic cells (normal cells) were incubated with α-DTPEBBTD-C4 based AIE-dots at increasing concentrations (1-12 nM) for 48 hours (see below). Cellular toxicity study reveals very low cytotoxicities of the AIE-dots against both cancer and normal cells (FIG. 7).

In vivo toxicity of AIE-dots was also evaluated by intravenous injection of the AIE-dots into healthy mice, in which the dots concentration for assessment of in vivo toxicity (100 nM) is two times higher than that used for the following image-guided surgery experiment (see below). Further data including mouse body weight changes over time and the blood chemistry tests on day 9 post AIE-dots administration indicate that our AIE-dots lead to no observable in vivo toxicity.

Cytotoxicity Study.

MTT assays were employed to evaluate the cytotoxicities of AIE-dots against both cancer and normal cells. In brief, 4T1 cancer cells and L02 hepatic cells were seeded in 96-well plates (Costar, Ill., USA) at a density of $4 \times 10^4$ cells/mL, respectively. After 24 h incubation, both the cells were exposed to a series of doses of AIE-dots. At 48 h post addition of AIE-dots, the wells were washed with 1×PBS buffer and 100 μL of freshly prepared MTT solution (0.5 mg/mL) in culture medium was added into each well. The MTT medium solution was carefully removed after 3 h incubation in the incubator. DMSO (100 μL) was then added into each well and the plate was gently shaken for 10 min at room temperature to dissolve all the precipitates formed. The absorbance of MTT at 490 nm was then monitored by the microplate Reader (GENios Tecan). Cell viability was expressed by the ratio of the absorbance of cells incubated with AIE-dots to that of the cells incubated with culture medium only.

Study on Evaluation of In Vivo Toxicity.

Healthy BALB/c mice were randomly assigned to 2 groups and each group contained 4 mice. On day 0, the mice in one group were intravenously injected with 100 μL of AIE-dots (100 nM). After the injection, 9 day follow-up experiments were conducted, in which the weights of all the mice in two groups were scrutinized. On day 9, the mice in two groups were sacrificed and the blood was collected through cardiac puncture at the time of sacrifice for blood chemistry analyses by Tianjin First Central Hospital.

Example 6: Cell Imaging Study

In Vitro Cell Tracking:

RAW 264.7 cells were cultured in T25 flask and 8-well confocal imaging chambers to achieve 80% confluence using DMEM+10% FBS+1% P/S cell culture medium. VivoTrack 680 and NIR AIE dots in cell culture medium were then added to the flask and 8-well chamber respectively. After 4 h incubation, the cells were washed with 1×PBS. The cells in 8-well chamber were proceeding to fluorescence imaging studies using CLSM (Olympus FV1000, Jena, Germany). Cells in the T25 flask were further sub-cultured in 8-well confocal imaging chambers for fluorescence imaging studies at day 2 and day 3. The laser at 633 nm was adopted to obtain the fluorescence images with a 650IF nm bandpass filter.

Results.

Figure 8:
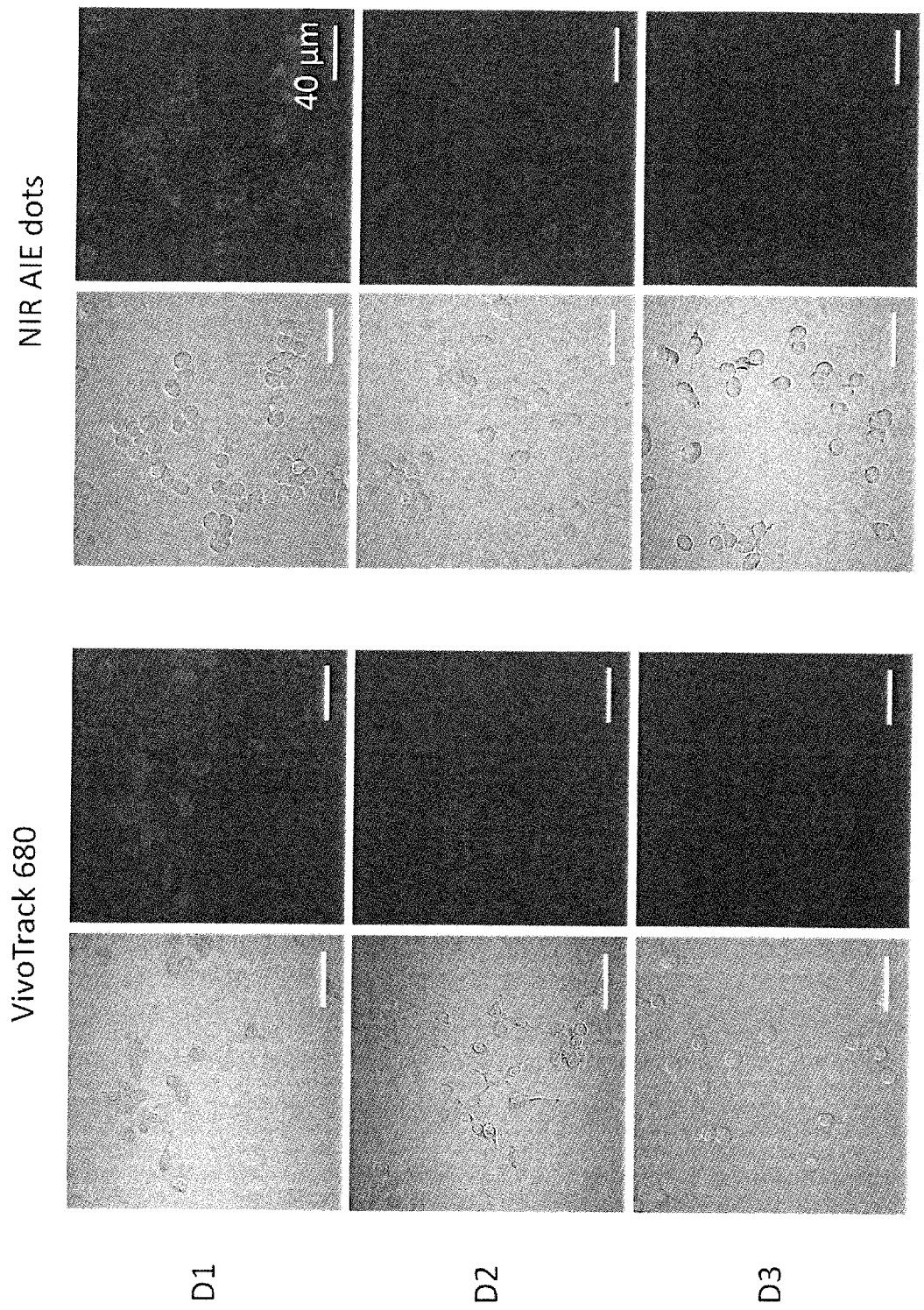
FIG. 8 depicts a comparison between AIE dots of the current disclosure and vivo-track 680 in cell tracking. Excitation wavelength: 633 nm, Emission: BA650IF filter.

Cell imaging results with the macrophage cell line (RAW 264.7) reveals that the AIE dots can track cells longer, as compared to the commercial cell trackers VivoTrack 680 from Perkin Elmer (FIG. 8). Excitation wavelength: 633 nm, Emission: BA650IF filter.

Example 7: Living Cell Imaging

Surgery with AIE-Dots Fluorescence Guidance.

The mice bearing peritoneal carcinomatosis were intravenously injected with 100 μL of AIE-dots (50 nM). At 24 h post-injection, the mice were anesthetized. The abdomen or thoracic cavity of mice was opened, followed by bioluminescence and fluorescence imaging during surgery. The excised tumor nodules were analyzed by both imaging modalities. Alternatively, the surgery was performed by the experience of a surgeon without imaging guidance (unguided). Bioluminescence imaging was performed using the Xenogen IVIS® Lumina II system post intraperitoneal injection of D-luciferin (150 mg/kg) into the mice. The bioluminescence signals were quantified in units of maximum photons per second per square centimeter per steridian. On the other hand, fluorescence imaging was carried out using a Maestro EX in vivo fluorescence imaging system (CRi, Inc.). The light with a central wavelength at 635 nm was selected as the excitation source. In vivo spectral imaging from 670 nm to 900 nm in 10 nm steps was conducted with an exposure time of 150 ms for each image frame. The original fluorescence images contained both signal and mouse autofluorescence were shown, which were not post-processed by any software, such as unmixing function of Maestro software, to remove the background fluorescence.

Results.

Figure 9:
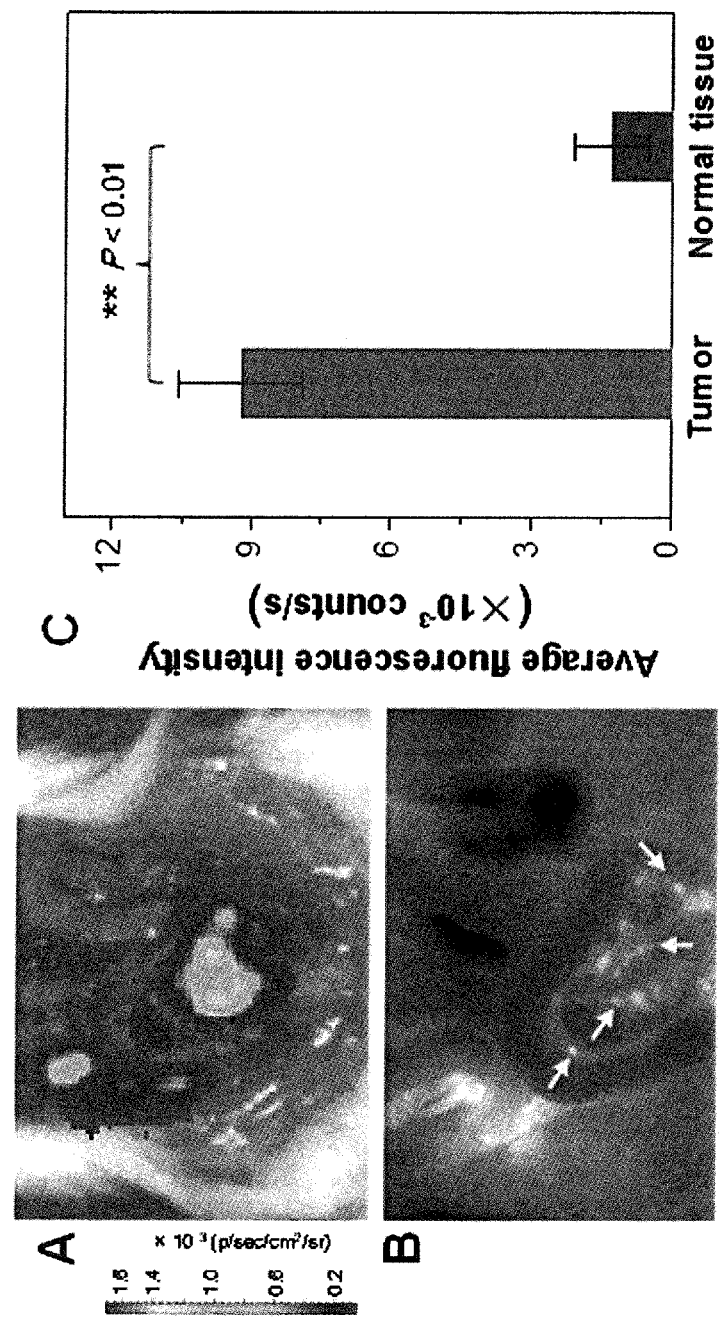

The promising results obtained in living cell imaging motivated us to further explore the feasibility of the AIE-dots for in vivo NIR fluorescence imaging. As shown in FIG. 9, it can be seen that our AIE-dots can be used to accurately identify the tumor location with a high tumor-to-normal tissue ratio of 7.2. Further results demonstrated that our AIE-dots can also be used for image-guided tumor surgery. These results make our AIE-dots promising for in vivo bioimaging.

The invention claimed is:

1. A compound of structural formula I:

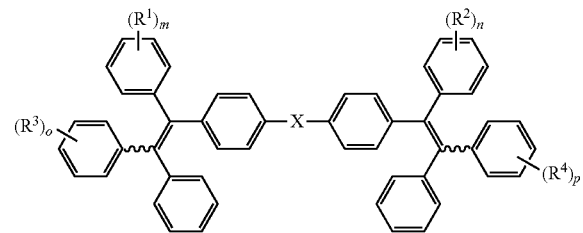

I wherein,

X represents an acceptor moiety selected from the group consisting of:

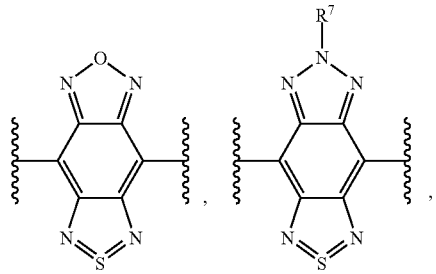

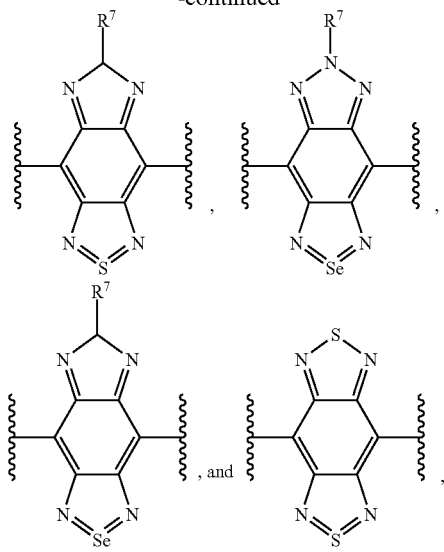

where each wavy line represents a point of attachment to the rest of the compound, and $R^7$ represents $C_{1-21}$ alkyl;
$R^1$ and $R^2$ independently represent $OR^5$ or $C_{1-21}$ alkyl;
$R^3$ and $R^4$ independently represent $OR^6$ or $C_{1-21}$ alkyl;
$R^5$ and $R^6$ independently represent $C_{1-21}$ alkyl;
m and n represent 0 or 1; and
o and p represent 0 or 1, provided that:
when m and n represent 0, o and p represent 1; and
when o and p represent 0, m and n represent 1.

2. The compound of claim 1, wherein, when present, each of $R^1$ to $R^4$ are attached to its respective phenyl ring in the ortho- or para-position relative to the point of attachment of said phenyl ring to the rest of the compound.

3. The compound of claim 2, wherein, when present, each of $R^1$ to $R^4$ are attached to its respective phenyl ring in the para-position relative to the point of attachment of said phenyl ring to the rest of the compound.

4. The compound of claim 1, wherein, when present, $R^1$ to $R^4$ and $R^7$ independently represent $C_{1-18}$ alkyl.

5. The compound of claim 4, wherein, when present, $R^1$ to $R^4$ and $R^7$ independently represent $C_{2-15}$ alkyl.

6. The compound of claim 1, wherein, when present, $R^5$ to $R^7$ independently represent $C_{1-18}$ alkyl.

7. The compound of claim 6, wherein, when present, $R^5$ to $R^7$ independently represent $C_{2-15}$ alkyl.

8. The compound of claim 1, wherein $R^1$ and $R^2$ are both $OR^5$ and o and p represent both 0.

9. The compound of claim 1, wherein the compound has structural formula II:

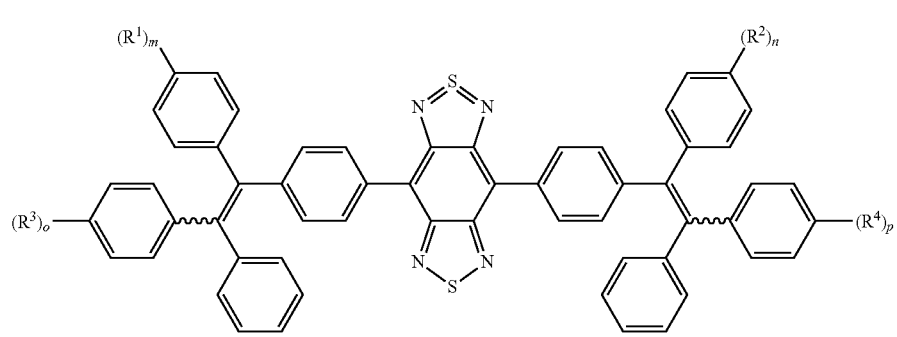

II wherein, $R^1$ to $R^4$, m, n, o and p are as defined in claim 1.
10. The compound of claim 1, wherein the compound is selected from:
i)
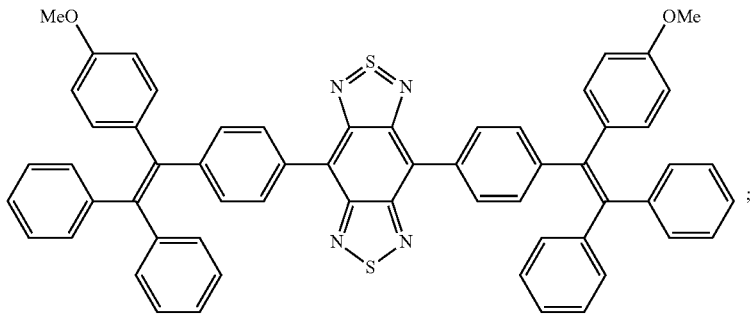
;
ii)
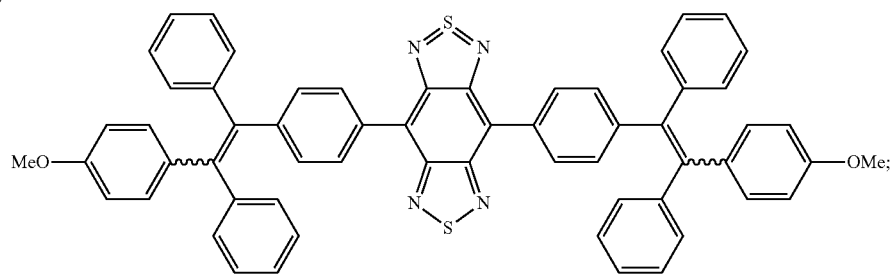
;
iii)
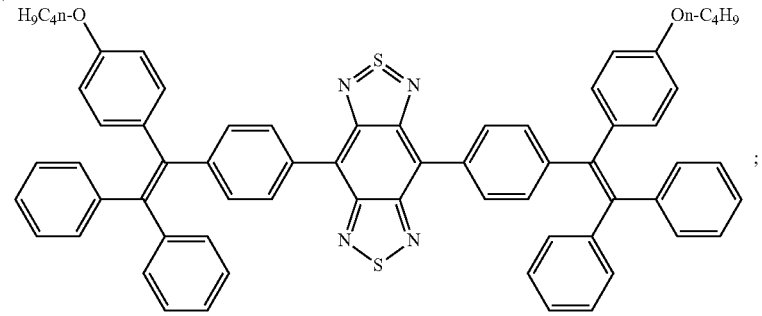
;
iv)
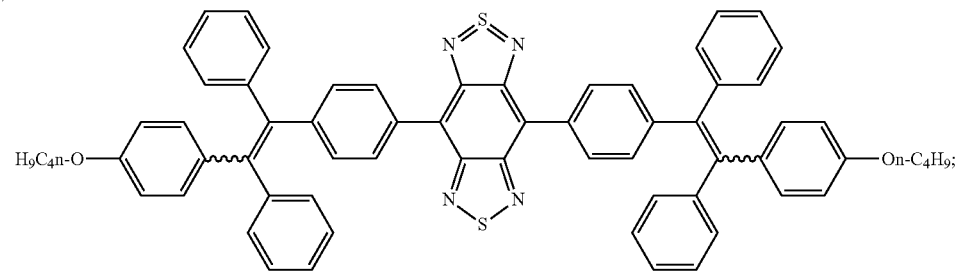
;
v)
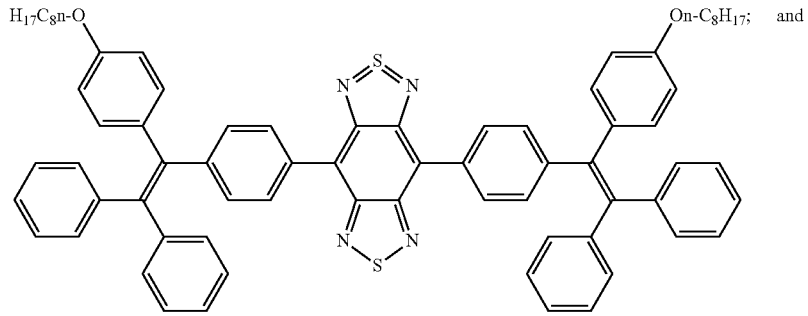
and vi)

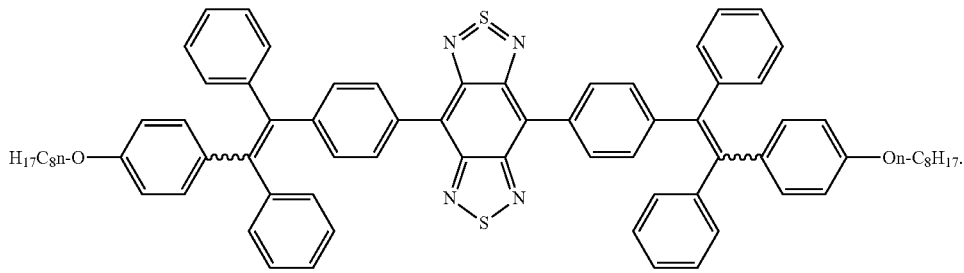

11. The compound of claim 10, wherein the compound is selected from:

i)

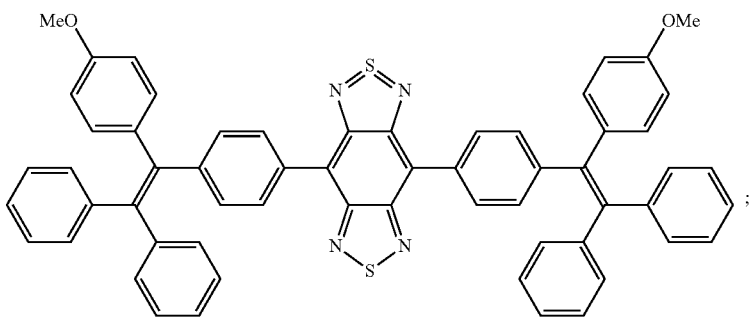

;

ii)

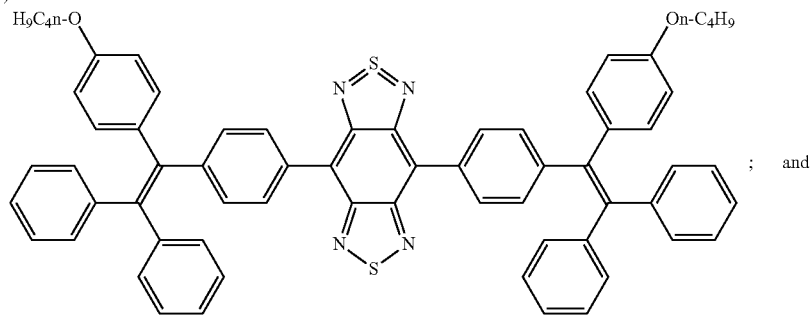

;  and iii)

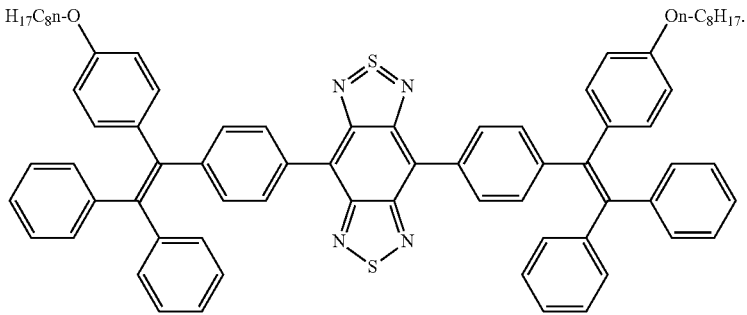

12. The compound according to claim 1 for use as an imaging agent for detecting cancer cells in a subject.

13. The compound according to claim 1 for use in the preparation of an in vivo imaging agent for detecting cancer cells in a subject.

14. A pharmaceutical composition comprising a compound according to claim 1 and a pharmaceutically acceptable carrier.

* * * * *